US008158125B2

(12) United States Patent
Naparstek et al.

(10) Patent No.: US 8,158,125 B2
(45) Date of Patent: *Apr. 17, 2012

(54) B-CELL EPITOPE PEPTIDES OF HSP 65, NOVEL AMINO ACID SEQUENCES, DNA ENCODING THE AMINO ACID SEQUENCES OF SAID PEPTIDES, ANTIBODIES DIRECTED AGAINST SAID PEPTIDES AND DIFFERENT USES THEREOF IN THE TREATMENT OF INFLAMMATORY AND AUTOIMMUNE DISEASES

(75) Inventors: Yaakov Naparstek, Jerusalem (IL); Rina Ulmansky, Jerusalem (IL); Yechezkei Kashi, Haifa (IL)

(73) Assignee: Hadasit Medical Research Services & Development Ltd., Jerusalem (IL)

(*) Notice: Subject to any disclaimer, the term of this patent is extended or adjusted under 35 U.S.C. 154(b) by 375 days.

This patent is subject to a terminal disclaimer.

(21) Appl. No.: 12/344,919

(22) Filed: Dec. 29, 2008

(65) Prior Publication Data

US 2009/0181028 A1    Jul. 16, 2009

Related U.S. Application Data

(63) Continuation-in-part of application No. 10/931,944, filed on Aug. 31, 2004, now Pat. No. 7,488,476, which is a continuation-in-part of application No. 10/853,567, filed on May 24, 2004, now Pat. No. 7,247,305, which is a continuation of application No. 09/847,637, filed on May 2, 2001, now Pat. No. 6,770,281, which is a continuation-in-part of application No. PCT/IL99/00595, filed on Nov. 4, 1999.

(60) Provisional application No. 60/107,213, filed on Nov. 5, 1998.

(51) Int. Cl.
*A61K 39/395* (2006.01)
(52) U.S. Cl. ............... 424/139.1; 424/133.1; 424/150.1; 514/6.9; 514/16.6
(58) Field of Classification Search .................. None
See application file for complete search history.

(56) References Cited

U.S. PATENT DOCUMENTS

| | | | |
|---|---|---|---|
| 5,114,844 A | 5/1992 | Cohen et al. | |
| 5,780,034 A | 7/1998 | Cohen et al. | |
| 5,985,287 A | 11/1999 | Tan et al. | |
| 6,770,281 B2 | 8/2004 | Naparstek et al. | |
| 7,247,305 B2 | 7/2007 | Naparstek et al. | |
| 7,488,476 B2 | 2/2009 | Naparstek et al. | |

FOREIGN PATENT DOCUMENTS

| | | |
|---|---|---|
| WO | 95/25744 A1 | 9/1995 |
| WO | 96/10039 A1 | 4/1996 |
| WO | 00/27870 | 5/2000 |

OTHER PUBLICATIONS

Fabris et al., Haematologica. Jan. 2000;85(1):72-81.*
Blazar et al., Blood. Feb. 1, 1995;85(3):842-51.*
Tamura et al., Pharm Res. Aug. 1996;13(8):1213-8.*
Khachigian et al., J Immunol Methods. Jul. 5, 1991;140(2):249-58.*
International Search Report published May 18, 2000 for PCT/IL1999/00595.
www.infoplease.com/dictionary/immunity, downloaded Mar. 23, 2006, 2 pages.
www.onelook.com/?other=web1931&w=immunity, downloaded Mar. 23, 2006, 1 page.
K. G. Warren et al., Fine specificity of the antibody response to myelin basic protein in the central nervous system in multiple sclerosis: The minimal B-cell epitope and a model of its features, Proc. Natl. Acad. Sci., 1995, pp. 11061-11065, vol. 92, USA.
Dana Elias et al., Peptide therapy for diabetes in NOD mice, Lancet, 1994, pp. 704-706, vol. 343.
Dana Elias et al., The hsp60 Peptide p277 Arrests the Autoimmune Diabetes Induced by the Toxin Streptozotocin, Diabetes, Sep. 1996, pp. 1168-1172, vol. 45.
S.C. Jordan et al., Treatment of autoimmune diseases and systemic vasculitis with pooled human intravenous immune globulin, M. Clin. Exp. Immunol., 1994, pp. 31-38, vol. 97.
Wei Chen et al., Human 60-kDa Heat-Shock Protein: A Danger Signal to the Innate Immune System, The Journal of Immunology, 1999, pp. 3212-3219, vol. 162.
Seth Lederman et al., A Single Amino Acid Substitution in a Common African Allele of the CD4 molecule Ablates Binding of the Monoclonal Antibody, OKT4, Molecular Immunology, 1991, pp. 1171-1181, vol. 28.
Marc H. V. Van Regenmortel, Mapping Epitope Structure and Activity: From One-Dimensional Prediction to Four-Dimensional Description of Antigenic Specific, Methods: a companion to Methods in Enzymology, 1996, pp. 465-472, vol. 9, No. 0054. Choh Hao Li et al., Beta-Endorphin Omission Analogs: Dissociation of Immunoreactivity from other Biological Activities, Proc. Natl. Acad. Sci., Biochemestry, Jun. 1980, pp. 3211-3214, vol. 77, No. 6 USA.
Maria Giovanna Danieli et al., Antibodies to Mycobacterial 65 kDa Heat Shock Protein in Systemic Sclerosis (Scleroderma), Journal of Autoimmunity, 1992, pp. 443-452, vol. 5.
P. M. Colman, Research in Immunology, 1994, pp. 33-36, vol. 145, No. 1.
Pierce, www.piercenet.com/products/browse: "Crosslinking Reagents", downloaded from piercenet.com on Mar. 24, 2006, 2 pages.

(Continued)

*Primary Examiner* — Michael Szperka
(74) *Attorney, Agent, or Firm* — Martin Fleit; Paul D. Bianco; Fleit Gibbons Gutman Bongini & Bianco PL

(57) ABSTRACT

B-cell epitope peptides of HSP 65, particularly the peptides comprising the amino acid sequence substantially as denoted by SEQ ID: NOs. 1-5 and their biologically functional homologues and derivatives thereof. Also included are polyclonal and monoclonal antibodies directed against them and their compositions for passive immunization against inflammatory and autoimmune diseases and in the treatment of inflammatory and autoimmune diseases. Also encompassed are diagnostic uses of these antibodies, for identifying people at risk of developing arthritis or diabetes, and a method of monitoring progress of the disease conditions and disease prognosis.

13 Claims, 12 Drawing Sheets

OTHER PUBLICATIONS

Chengfend Xiao et al., Expression of the 60 kDa and 71 kDa heat shock proteins and presence of antibodies against the 71 kDa heat shock protein in pediatric patients with immune thrombocytopenic purpura, BMC Blood Disorders, Mar. 2004, pp. 1-10, vol. 4, No. 1.

R. Astarloa et al., Humoral response to the Human heat shock 60 kDa protein in myasthenia gravis, Journal of the Neurological Sciences, 1996, pp. 182-183, vol. 135.

Charles A. Janeway, Jr. et al., Immuno Biology The Immune System in Health and Disease, Third Edition, 1997 8:2-8:7.

Lubert Stryer, Biochemistry Fourth Edition, W.H. Freeman and Company, Second printing 1995, KP; Chapter 3, pp. 53-58.

Jose Antonio Lopez-Guerrero et al., Modulation of Adjuvant Arthritis in Lewis Rats by Recombinant Vaccinia Virus Expressing the Human 60-Kilodalton Heat Shock Protein, Infection and Immunity, Oct. 1993, pp. 4225-4231, vol. 61, No. 10.

James H. McKerrow, Non-Enzymatic, Post-Translational, Amino Acid Modifications in Ageing. A Brief Review, J.H. Mechanisms of Ageing and Development, 1979, pp. 371-377, vol. 10.

H Tonie Wright, Nonenzymatic Deamidation of Asparaginyl and Glutaminyl Residues in proteins, Critical Reviews in Biochemistry and Molecular Biology, 1991, pp. 1-52, vol. 26, No. 1.

Pierce; www.piercenet.com/products/browse: "Amino Acid Side Chain Modification Agents", downloaded from piercenet.com on Mar. 24, 2006, 2 pages.

Joseph Holoshitz et al., Lines of T Lymphocytes Induce or Vaccinate Against Autoimmune Arthritis, Science, 1983, pp. 56-58, vol. 219.

Joseph Holoshitz et al., T Lymphocytes of Rheumatoid Athritis Patients Show Augmented Reactivity to a Fraction of Mycobacteria Cross-Reactive with Cartilage, Lancet, Aug. 1986, pp. 305-309, vol. 2.

Pieter C. M. Res et al., Synovial Fluid T Cell Reactivity Against 65kD Heat Shock Protein of Mycobacteria in Early Chronic Arthritis, Lancet, Aug. 27, 1988, pp. 478-480, vol. 2.

J. S. Gaston et al., In Vitro Responses to a 65-Kilodalton Mycobacterial Protein by Synovial T Cells from Inflammatory Arthritis Patients, The Journal of Immunology, Oct. 15, 1989, pp. 2494-2500, vol. 143, No. 8.

J. S. Gaston et al., Recognition of a Mycobacteria-Specific Epitope in the 65-kD Heat-Shock Protein by Synovial Fluid-Derived T Cell Clones, J. Exp. Med., 1990, pp. 831-841, vol. 171.

Alison J. Quayle et al., Peptide recognition, T cell receptor usage and HLA restriction elements of human heat-shock protein (hsp) 60 and mycobacterial 65-kDa hsp-reactive T cell clones from rheumatoid synovial fluid, Eur. J. Immunol., 1992, pp. 1315-1322, vol. 22.

Judy Henwood et al., Restricted T cell receptor expression by human T cell clones specific for mycobacterial 65-kDa heat-shock protein: selective in vivo expansion of T cell bearing defined receptors, Eur. J. Immunol., 1993, pp. 1256-1265, vol. 23.

M. E. J. Billingham et al., A Mycobacterial 65-kD Heat Shocl Protein Induces Antigen-Specific Suppression of Adjuvant Arthritis, but is not itself Arthritogenic, J. Exp. Med., Jan. 1990, pp. 339-344, vol. 171.

Els J. M. Hogervorst et al., Adjuvant arthritis and immunity to the mycobacterial 65 kDa heat shock protein, International Immunology, 1992, pp. 719-727, vol. 4, No. 7.

X. D. Yang et al., Prevention of adjuvant arthritis in rats by a nonapeptide from the 65-kD mycobacterial heat-shock protein, Clin. Exp. Immunol., 1990, pp. 189-194, vol. 81.

J.S. Friedland et al., Mycobacterial 65-kD heat shock protein induces release of proinflammatory cytokines from human monocytic cells, Clin. Exp. Immunol., 1993, pp. 58-62, vol. 91.

Stephen M. Anderton et al., Differential Mycobacterial 65-kDa Heat Shocl Protein T Cell Epitope Recognition after Adjuvant Arthritis-Inducing or Protective Immunization Protocols, The American Association of Immunologies, J. Immunol., 1994, pp. 3656-3664, vol. 152.

Kamal D. Moudgil et al., Diversification of T Cell Responses to Carboxy-terminal Determinants within the 65-kD Heat-shock Protein is Involved in Regulation of Autoimmune Arthritis, J. Exp. Med., 1997, pp. 1307-1316, vol. 185.

Satish Jindal et al., Primary Structure of a Human Mitochondrial Protein Homologous to the Bacterial and Plant Chaperonins and to the 65-Kilodalton Mycobacterial Antigen, Mol. Cell. Biol., 1989, pp. 2279-2283, vol. 9.

S. Kleinau et al., A Monoclonal Antibody to the Mycobacterial 65kDa Heat Shock Protein (ML 30) Binds to Cells in Normal and Arthritic Joints of Rats, Scand. J. Immunol., 1991, pp. 195-202, vol. 33.

Martin R. Munk et al., T lymphocytes from healthy individuals with specificity to self-epitopes shared by the mycobacterial and human 65-kilodalton heat shock protein, The Journal of Immunology, The American Association of Immunologists, Nov. 1989, pp. 2844-2849, vol. 143.

S. M. Anderton et al., Inflammation activates self hsp60-specific T cells, Eur. J. Immunol., 1993, pp. 33-38, vol. 23.

D. H. Margulies et al., Antibody Detection and Preparation, Current Protocols in Immunology, 1996, pp. 2.0.1-2.13.16.

Philip G. Kasprzyk et al., Solid-Phase Peptide Quantitation Assay Using Labeled Monoclonal Antibody and Glutaraldehyde Fixation, Analytical Biochemistry, 1988, pp. 224-234, vol. 174.

Pierce; www.piercenet.com/products/browse: "Protein Modification Reagents", downloaded from piercenet.com on Mar. 24, 2006, 4 pages.

Pierce; www.piercenet.com/products/browse: "Introduction to CrossLinking", downloaded from piercenet.com on Mar. 24, 2006, 10 pages.

Roger J. Booth et al., The use of a 'universal' yeast expression vector to produce an antigenic protein of *Mycobacterium leprae*, Immunology Letters, 1988, pp. 65-69, vol. 19.

Bill L. Brizzard et al., Immunoaffinity Purification of FLAG Epitope-Tagged Bacterial Alkaline Phosphatase Using a Novel Monoclonal Antibody and peptide Elution, BioTechniques, 1996, pp. 730-734, vol. 16, No. 4.

Linda S. Wicker et al., Type 1 diabetes genes and pathways shared by humans and NOD mice, Journal of Autoimmunity, 2005, pp. 29-33, vol. 25.

Marian F. Young, Mouse models of osteoarthritis provide new research tools, Trends in Pharmacological Sciences, 2005, pp. 333-335, vol. 26.

Brett D. Noerager et al., An IgM anti-MBP Ab in a case of Waldenstrom's macroglobulinemia with polyneuropathy expressing an idiotype reactive with an MBP epitope immunodominant in MS and EAE, Journal of Neuroimmunology, 2001, pp. 163-169, vol. 113.

R. M. Mason et al., The STR/ort mouse and its use as a model of osteoarthritis, Osteoarthritis and Cartilage, Journal of the OsteoArthritis Research Society International, 2001, pp. 85-91, vol. 9.

Laurent G Ameye et al., Animal models of osteoarthritis: lessons learned while seeking the 'Holy Grail', Curr. Opin. Rheumatol, 2006, pp. 537-547, vol. 18.

Wim B. Van Den Berg, PhD, Lessons from animal models of osteoarthritis, Current Opinion in Rheumatology, 2001, pp. 452-456, vol. 13.

Carl M. Pearson, Development of Arthritis, Periarthritis and Periostitis in Rats Given Adjuvants, C.M. Proc. Soc. Exp. Biol. Med., 1956, pp. 95-101, vol. 91.

Carl M. Pearson et al., Studies of Polyarthritis and Other Lesions Induced in Rats by Injection of Mycobacterial Adjuvant. I. General Clinical and Pathologic Characteristics and Some Modifying Factors, C.M. & Wood, F.D. Arthritis Rheum., 1959, pp. 440-459, vol. 2.

Stephen M. Anderton et al., Activation of T Cells recognizing Self 60-kD Heat Shock protein Can protect against Experimental Arthritis, J. Exp. Med., Mar. 1995, pp. 943-952, vol. 181.

Steinitz, M. Human Monoclonal Antibodies Produced by Epstein-Barr Virus Immortalized Cell Lines: Technical and Theoretical Principles, Monoclonal Antibodies from EBV Immortalized Cell Lines, Reviews on Immunoassay Technology, 2: 1-16 (1988).

Rina Ulmansky, Resistance to Adjuvant Arthritis is Due to Protective Antibodies Against Heat Shock Protein Surface Epitopes and the Induction of IL-10 Secretion, The Journal of Immunology, 2002, pp. 6463-6469, vol. 168.

Anibal Cravchik et al., A novel strategy for the immunological tagging of cDNA constructs, Gene, 1993, pp. 139-143, vol. 137.

Andrew J. Rowan et al., Introduction of a myc Reporter tag to Improve the Queality of Mutation Detection Using the Protein Truncation Test, Methods, Human Mutation, 1997, pp. 172-176, vol. 9.

Alfred D. Steinberg et al., Timing of Immunosuppression in the Natural History of Autoimmune Diseases, Journal of Autoimmunity, 1992, 5 Supplement A, pp. 197-203, abstract only.

Jelle R. Thole et al., Characterization, Sequence Determination, and Immunogenicity of a 64-Kilodalton Protein of *Mycobacterium bovis* BCG Expressed in *Escherichia coli* K-12, Infection and Immunity, Jun. 1987, pp. 1466-1475, vol. 55, No. 6.

Rachel A. Craven et al., Vector for the expression of tagged proteins in *Schizosaccharomyces pombe*, Gene, An International Journal on Genes and Genomes, 1998, pp. 59-68, vol. 221.

Ofer Lider et al., Therapeutic vaccination against adjuvant arthritis using autoimmune T cells treated with hydrostatic pressure, Proc. Natl. Acad. Sci., Immunology, Jul. 1987, pp. 4577-4580, vol. 84.

Berent J. Prakken et al., Heat Shock Protein 60 and adjuvant arthritis: a model for T cell regulation in human arthritis, Springer Seminars in Immunology, 2003, pp. 47-63, vol. 25.

Linda K. Myers et al., Collagen-Induced Arthritis, an animal model of autoimmunity, Life Sciences, 1997, pp. 1861-1878, vol. 61, No. 19.

David D. Brand et al., Immunopathogenesis of Collagen Arthritis, Springer Seminars in Immunopathology, 2003 3-18, vol. 25.

T. Bongartz et al., Treatment of active psoriatic arthritis with the PPAR gamma ligand pioglitazone: an open-label pilot study, Rheumatology, 2004, pp. 126-129, vol. 44, No. 1.

Masayuki Amagai, Autoimmunity against desmosomal cadherins in pemphigus, Journal of Dermatological Science, 1999, pp. 92-102, vol. 20.

Stephen R. Tan et al., Pemphigus Vulgaris Induced by Electrical Injury, Continuing Medical Education, 2006, pp. 161-165, vol. 77.

Charles A. Janeway, Jr. et al., Immunobiology, The Immune System in Health and Disease, 3rd ed., 1997, Garland Press, p. 11:11.

Berent J. Prakken et al., Peptide-induced nasal tolerance for a mycobacterial heat shock protein 60 T cell epitope in rats suppresses both adjuvant arthritis and nonmicrobially induced experimental arthritis, Proc. Natl. Acad. Sci., Medical Science, USA, 1997, pp. 3284-3289, vol. 94.

Xiao-Dong Yang et al., Treatment of Adjuvant Arthritis in Rats: Vaccination Potential of a Synthetic Nonapeptide from the 65kD Heat Shock Protein of Mycobacteria, Journal of Autoimmunity, 1990, pp. 11-23, vol. 3.

Mark H. Beers, M.D., et al., The Merck Manual of Diagnosis and Therapy, 17th ed., Merck Research laboratories, 1999, pp. 96-99, 165-177, 409-423, 445-447, 449-451, 455-459, 922-925, 1291-1295, 1475-1477, 1496-1499, and 2041-2045.

Natalia Lopez-Mortalla et al., A common structural motif in immunopotentiating peptides with sequences present in human autoantigens. Elicitation of a response mediated by monocytes and Th1 cells, Biochemica Biophysica Acta, 1996, pp. 183-191, vol. 1317.

Berent Prakken et al., Nasal administration of arthritis-related T cell epitopes of heat shock protein 60 as a promising way for immunotherapy in chronic arthritis, Biotherapy, 1998, pp. 205-211, vol. 10.

R. N. Barker et al., Differential Effects of Immunisation with Mycobacterial 65 kD Heat Shock Protein on Two Models of Autoimmunity, Autoimmunity, 1992, pp. 73-77, vol. 14.

W. Lee Maloy et al., Production of Antipeptide Antisera, Current Protocols in Immunology, 2000, pp. 9.4.1-9.4.12, vol. 39.

M. Ghoraishian et al., Comparison between the protective effects of mycobacterial 65-kD heat shock protein and ovomucoid in pristane-induced arthritis: relationship with agalactosyl IgG, Clin. Exp. Immunol., 1993, pp. 247-251, vol. 94.

Els J. M. Hogervorst et al., Modulation of Experimental Autoimmunity: Treatment of Adjucant Arthritis by Immunization with a Recombinant Vaccinia Virus, Infection and Immunity, Jun. 1991, pp. 2029-2035, vol. 59, No. 6.

Byron H. Waksman et al., Passive Transfer of Adjuvant Arthritis in rats with Living Lymphoid Cells of Sensitized Donors, C. Int. Arch. Allergy, 1963, pp. 129-139, vol. 23.

Rina Ulmansky et al., Immunoglobulin from rats that are resistant to adjuvant arthritis suppress the disease in arthritis-susceptible rats, Eur. J. Immunol., 1995, pp. 952-957, vol. 25.

E. J. M. Hogervorst et al., T cell reactivity to an epitope of the mycobacterial 65-kDa heat-shock protein (hsp 65) corresponds with arthritis susceptibility in rats and is regulated by hsp 65-specfic cellular responses, Eur. J. Immunol., 1991, pp. 1289-1296, vol. 21.

Marie M. Griffiths et al., Induction of Autoimmune Arthritis in Rats by Immunization with Homologous Rat Type II Collagen is Restricted to the RT1 av1 Haplotype, Arthritis and Rheumatism, pp. 254-258, vol. 36, 2003.

Williem Van Eden et al., Cloning of the mycobacterial epitope recognized by T lymphocytes in adjuvant arthritis Nature, 1988, pp. 171-173, vol. 331.

* cited by examiner

```
                                          1          6                    25
HSP 65 - M.T.     ----------  ----------  ------MAKTI AYDEEARRGL ERGLNALADA
HSP 60 - RAT      MLRLPTVLRQ  MRPVSRALAP  HLTRAYAKDV  KFGADARALM LQGVDLLADA
HSP 60 - HUMAN    MLRLPTVFRQ  MRPVSRVLAP  HLTRAYAKDV  KFGADARALM LQGVDLLADA

Consensus         ----------  ----------  ------AK--  -----AR--- --G---LADA 26                                                    75
HSP 65 - M.T.     VKVTLGPKGR  NVVLEKKWGA  PTITNDGVSI  AKEIELEDPY EKIGAELVKE
HSP 60 - RAT      VAVTMGPKGR  TVIIEQSWGS  PKVTKDGVTV  AKSIDLKDKY KNIGAKLVQD
HSP 60 - HUMAN    VAVTMGPKGR  TVIIEQSWGS  PKVTKDGVTV  AKSIDLKDKY KNIGAKLVQD Consensus         V-VT-GPKGR  -V--E--WG-  P--T-DGV--  AK-I-L-D-Y --IGA-LV--
                         [6-7(31-52 AA)]

76                                                   125
HSP 65 - M.T.     VAKKTDDVAG  DGTTTATVLA  QALVREGLRN  VAAGANPLGL KRGIEKAVEK
HSP 60 - RAT      VANNTNEEAG  DGTTTATVLA  RSIAKEGFEK  ISKGANPVEI RRGVMLAVDA
HSP 60 - HUMAN    VANNTNEEAG  DGTTTATVLA  RSIAKEGFEK  ISKGANPVEI RRGVMLAVDA

Consensus         VA--T---AG  DGTTTATVLA  -----EG---  ---GANP--- -RG---AV--
                                                                [21 (121-136 AA)]

126                                                  174
HSP 65 - M.T.     VTETLLKGAK  EVETKEQIAA  TAAISA.GDQ  SIGDLIAEAM DKVGNEGVIT
HSP 60 - RAT      VIAELKKQSK  PVTTPEEIAQ  VATISANGDK  DIGNIISDAM KKVGRKGVIT
HSP 60 - HUMAN    VIAELKKQSK  PVTTPEEIAQ  VATISANGDK  EIGNIISDAM KKVGRKGVIT

Consensus         V---L-K--K  -V-T-E-IA-  -A-ISA-GD-  -IG--I--AM -KVG--GVIT 175                                                  224
HSP 65 - M.T.     VEESNTFGLQ  LELTEGMRFD  KGYISGYFVT  DPERQEAVLE DPYILLVSSK
HSP 60 - RAT      VKDGKTLNDE  LEIIEGMKFD  RGYISPYFIN  TSKGQKCEFQ DAYVLLSEKK
HSP 60 - HUMAN    VKDGKTLNDE  LEIIEGMKFD  RGYISPYFIN  TSKGQKCEFQ DAYVLLSEKK Consensus         V----T----  LE--EGM-FD  -GYIS-YF--  ----Q----- D-Y-LL---K
                              [31 (181-196 AA)]                 [36 (211-226 AA)]

225                                                  274
HSP 65 - M.T.     VSTVKDLLPL  LEKVIGAGKP  LLIIAEDVEG  EALSTLVVNK IRGTFKSVAV
HSP 60 - RAT      ISSVQSIVPA  LEIANAHRKP  LVIIAEDVDG  EALSTLVLNR LKVGLQVVAV
HSP 60 - HUMAN    ISSIQSIVPA  LEIANAHRKP  LVIIAEDVDG  EALSTLVLNR LKVGLQVVAV

Consensus         -S------P-  LE------KP  L-IIAEDV-G  EALSTLV-N- -------VAV
                              [40 (236-251 AA)]              [45 (265-280 AA)]
```

Fig. 1

```
              275                                                          323
HSP 65 - M.T.  KAPGFGDRRK  AMLQDMAILT  GGQVISEE.V  GLTLENADLS  LLGKARKVVV
HSP 60 - RAT   KAPGFGDNRK  NQLKDMAIAT  GGAVFGEEGL  NLNLEDVQAH  DLGKVGEVIV
HSP 60 - HUMAN KAPGFGDNRK  NQLKDMAIAT  GGAVFGEEGL  TLNLEDVQPH  DLGKVGEVIV

Consensus      KAPGFGD-RK  --L-DMAI-T  GG-V--EE--  -L-LE-----  -LGK---V-V 324                                                          373
HSP 65 - M.T.  TKDETTIVEG  AGDTDAIAGR  VAQIRQEIEN  SDSDYDREKL  QERLAKLAGG
HSP 60 - RAT   TKDDAMLLKG  KGDKAHIEKR  IQEITEQLDI  TTSEYEKEKL  NERLAKLSDG
HSP 60 - HUMAN TKDDAMLLKG  KGDKAQIEKR  IQEIIEQLDV  TTSEYEKEKL  NERLAKLSDG Consensus      TKD------G  -GD---I--R  ---I------  --S-Y--EKL  -ERLAKL--G
                                                  59 (349-364 AA)

374                                                          423
HSP 65 - M.T.  VAVIKAGAAT  EVELKERKHR  IEDAVRNAKA  AVEEGIVAGG  GVTLLQAAPT
HSP 60 - RAT   VAVLKVGGTS  DVEVNEKKDR  VTDALNATRA  AVEEGIVLGG  GCALLRCIPA
HSP 60 - HUMAN VAVLKVGGTS  DVEVNEKKDR  VTDALNATRA  AVEEGIVLGG  GCALLRCIPA

Consensus      VAV-K-G---  -VE--E-K-R  --DA-----A  AVEEGIV-GG  G--LL---P-
               63 (373-388 AA)

424                                                          472
HSP 65 - M.T.  LDELK.LEGD  EATGANIVKV  ALEAPLKQIA  FNSGLEPGVV  AEKVRNLPAG
HSP 60 - RAT   LDSLKPANED  QKIGIEIIKR  ALKIPAMTIA  KNAGVEGSLI  VEKILQSSSE
HSP 60 - HUMAN LDSLTPANED  QKIGIEIIKR  TLKIPAMTIA  KNAGVEGSLI  VEKIMQSSSE

Consensus      LD-L-----D  ---G--I-K-  -L--P---IA  -N-G-E----  -EK-------

473                                                          522
HSP 65 - M.T.  HGLNAQTGVY  EDLLAAGVAD  PVKVTRSALQ  NAASIAGLFL  TTEAVVADKP
HSP 60 - RAT   VGYDAMLGDF  VNMVEKGIID  PTKVVRTALL  DAAGVAPLLT  TAEAVVTEIP
HSP 60 - HUMAN VGYDAMAGDF  VNMVEKGIID  PTKVVRTALL  DAAGVASLLT  TAEVVVTEIP

Consensus      -G--A--G--  ------G--D  P-KV-R-AL-  -AA--A-L--  T-E-VV---P
                                                  84 (499-514 AA)

523         540
HSP 65 - M.T.  EKEKASVPGG  GDMGGMDF~~  ~~~~~
HSP 60 - RAT   KEEKD..PGM  GAMGGMGGGM  GGGMF
HSP 60 - HUMAN KEEKD..PGM  GAMGGMGGGM  GGGMF

Consensus      --EK---PG-  G-MGGM----  -----
```

Fig. 1 (continued)

The "Protective" Motif

| | |
|---|---|
| MT HSP Peptide 6- (31-46) | G P K G R N V V L E K K W G A P |
| MT HSP Peptide 7- (37-52) | V V L E E K K W G A P T I T N D G |
| Rat HSP Peptide 5- (36-55) | T V I I E Q S W W G S P K V T K D G V T V |

Common Motif   V = = E - - W G - P

Fig. 5

```
                              SEQUENCE LISTING

<160> NUMBER OF SEQ ID NOS: 25

<210> SEQ ID NO 1
<211> LENGTH: 22
<212> TYPE: PRT
<213> ORGANISM: Mycobacterium tuberculosis

<400> SEQUENCE: 1

Gly Pro Lys Gly Arg Asn Val Val Leu Glu Lys Lys Trp Gly Ala Pro
1               5                   10                  15

Thr Ile Thr Asn Asp Gly
            20

<210> SEQ ID NO 2
<211> LENGTH: 16
<212> TYPE: PRT
<213> ORGANISM: Mycobacterium tuberculosis

<400> SEQUENCE: 2

Gly Pro Lys Gly Arg Asn Val Val Leu Glu Lys Lys Trp Gly Ala Pro
1               5                   10                  15

<210> SEQ ID NO 3
<211> LENGTH: 16
<212> TYPE: PRT
<213> ORGANISM: Mycobacterium tuberculosis

<400> SEQUENCE: 3

Val Val Leu Glu Lys Lys Trp Gly Ala Pro Thr Ile Thr Asn Asp Gly
1               5                   10                  15

<210> SEQ ID NO 4
<211> LENGTH: 20
<212> TYPE: PRT
<213> ORGANISM: Homo sapiens

<400> SEQUENCE: 4

Thr Val Ile Ile Glu Gln Ser Trp Gly Ser Pro Lys Val Thr Lys Asp
1               5                   10                  15

Gly Val Thr Val
            20

<210> SEQ ID NO 5
<211> LENGTH: 67
<212> TYPE: DNA
<213> ORGANISM: Mycobacterium tuberculosis

<400> SEQUENCE: 5
gccgccatgg gaccaaaggg acgcaacgtg gtactagaga agaaatgggg cgcgccgtag      60
ctcgaga                                                               67

<210> SEQ ID NO 6
<211> LENGTH: 540
<212> TYPE: PRT
<213> ORGANISM: Mycobacterium tuberculosis

<400> SEQUENCE: 6

Met Ala Lys Thr Ile Ala Tyr Asp Glu Glu Ala Arg Arg Gly Leu Glu
```

-continued

```
1               5                   10                  15
Arg Gly Leu Asn Ala Leu Ala Asp Ala Val Lys Val Thr Leu Gly Pro
                20                  25                  30

Lys Gly Arg Asn Val Val Leu Glu Lys Lys Trp Gly Ala Pro Thr Ile
            35                  40                  45

Thr Asn Asp Gly Val Ser Ile Ala Lys Glu Ile Glu Leu Glu Asp Pro
        50                  55                  60

Tyr Glu Lys Ile Gly Ala Glu Leu Val Lys Val Ala Lys Lys Thr
65                  70                  75                  80

Asp Asp Val Ala Gly Asp Gly Thr Thr Thr Ala Thr Val Leu Ala Gln
                85                  90                  95

Ala Leu Val Arg Glu Gly Leu Arg Asn Val Ala Ala Gly Ala Asn Pro
            100                 105                 110

Leu Gly Leu Lys Arg Gly Ile Glu Lys Ala Val Glu Lys Val Thr Glu
        115                 120                 125

Thr Leu Leu Lys Gly Ala Lys Glu Val Glu Thr Lys Glu Gln Ile Ala
    130                 135                 140

Ala Thr Ala Ala Ile Ser Ala Gly Asp Gln Ser Ile Gly Asp Leu Ile
145                 150                 155                 160

Ala Glu Ala Met Asp Lys Val Gly Asn Glu Gly Val Ile Thr Val Glu
                165                 170                 175

Glu Ser Asn Thr Phe Gly Leu Gln Leu Glu Leu Thr Glu Gly Met Arg
            180                 185                 190

Phe Asp Lys Gly Tyr Ile Ser Gly Tyr Phe Val Thr Asp Pro Glu Arg
        195                 200                 205

Gln Glu Ala Val Leu Glu Asp Pro Tyr Ile Leu Leu Val Ser Ser Lys
    210                 215                 220

Val Ser Thr Val Lys Asp Leu Leu Pro Leu Leu Glu Lys Val Ile Gly
225                 230                 235                 240

Ala Gly Lys Pro Leu Leu Ile Ile Ala Glu Asp Val Glu Gly Glu Ala
                245                 250                 255

Leu Ser Thr Leu Val Val Asn Lys Ile Arg Gly Thr Phe Lys Ser Val
            260                 265                 270

Ala Val Lys Ala Pro Gly Phe Gly Asp Arg Arg Lys Ala Met Leu Gln
        275                 280                 285

Asp Met Ala Ile Leu Thr Gly Gly Gln Val Ile Ser Glu Glu Val Gly
    290                 295                 300

Leu Thr Leu Glu Asn Ala Asp Leu Ser Leu Leu Gly Lys Ala Arg Lys
305                 310                 315                 320

Val Val Val Thr Lys Asp Glu Thr Thr Ile Val Glu Gly Ala Gly Asp
                325                 330                 335

Thr Asp Ala Ile Ala Gly Arg Val Ala Gln Ile Arg Gln Glu Ile Glu
            340                 345                 350

Asn Ser Asp Ser Asp Tyr Asp Arg Glu Lys Leu Gln Glu Arg Leu Ala
        355                 360                 365

Lys Leu Ala Gly Gly Val Ala Val Ile Lys Ala Gly Ala Ala Thr Glu
    370                 375                 380

Val Glu Leu Lys Glu Arg Lys His Arg Ile Glu Asp Ala Val Arg Asn
385                 390                 395                 400

Ala Lys Ala Ala Val Glu Glu Gly Ile Val Ala Gly Gly Gly Val Thr
                405                 410                 415

Leu Leu Gln Ala Ala Pro Thr Leu Asp Glu Leu Lys Leu Glu Gly Asp
            420                 425                 430
```

```
Glu Ala Thr Gly Ala Asn Ile Val Lys Val Ala Leu Glu Ala Pro Leu
            435                 440                 445

Lys Gln Ile Ala Phe Asn Ser Gly Leu Glu Pro Gly Val Val Ala Glu
        450                 455                 460

Lys Val Arg Asn Leu Pro Ala Gly His Gly Leu Asn Ala Gln Thr Gly
465                 470                 475                 480

Val Tyr Glu Asp Leu Leu Ala Ala Gly Val Ala Asp Pro Val Lys Val
                485                 490                 495

Thr Arg Ser Ala Leu Gln Asn Ala Ala Ser Ile Ala Gly Leu Phe Leu
            500                 505                 510

Thr Thr Glu Ala Val Val Ala Asp Lys Pro Gly Lys Glu Lys Ala Ser
        515                 520                 525

Val Pro Gly Gly Gly Asp Met Gly Gly Met Asp Phe
    530                 535                 540

<210> SEQ ID NO 7
<211> LENGTH: 573
<212> TYPE: PRT
<213> ORGANISM: Rat

<400> SEQUENCE: 7

Met Leu Arg Leu Pro Thr Val Leu Arg Gln Met Arg Pro Val Ser Arg
1               5                   10                  15

Ala Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Asp Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Val Gln Ser
                245                 250                 255

Ile Val Pro Ala Leu Glu Ile Ala Asn Ala His Arg Lys Pro Leu Val
            260                 265                 270
```

```
Ile Ile Ala Glu Asp Val Asp Gly Glu Ala Leu Ser Thr Leu Val Leu
        275                 280                 285

Asn Arg Leu Lys Val Gly Leu Gln Val Ala Val Lys Ala Pro Gly
290                 295                 300

Phe Gly Asp Asn Arg Lys Asn Gln Leu Lys Asp Met Ala Ile Ala Thr
305                 310                 315                 320

Gly Gly Ala Val Phe Gly Glu Gly Leu Asn Leu Asn Leu Glu Asp
                325                 330                 335

Val Gln Ala His Asp Leu Gly Lys Val Gly Glu Val Ile Val Thr Lys
                340                 345                 350

Asp Asp Ala Met Leu Leu Lys Gly Lys Gly Asp Lys Ala His Ile Glu
                355                 360                 365

Lys Arg Ile Gln Glu Ile Thr Glu Gln Leu Asp Ile Thr Thr Ser Glu
370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                405                 410                 415

Lys Lys Asp Arg Val Thr Asp Ala Leu Asn Ala Thr Arg Ala Ala Val
                420                 425                 430

Glu Glu Gly Ile Val Leu Gly Gly Cys Ala Leu Leu Arg Cys Ile
                435                 440                 445

Pro Ala Leu Asp Ser Leu Lys Pro Ala Asn Glu Asp Gln Lys Ile Gly
450                 455                 460

Ile Glu Ile Ile Lys Arg Ala Leu Lys Ile Pro Ala Met Thr Ile Ala
465                 470                 475                 480

Lys Asn Ala Gly Val Glu Gly Ser Leu Ile Val Glu Lys Ile Leu Gln
                485                 490                 495

Ser Ser Ser Glu Val Gly Tyr Asp Ala Met Leu Gly Asp Phe Val Asn
                500                 505                 510

Met Val Glu Lys Gly Ile Ile Asp Pro Thr Lys Val Val Arg Thr Ala
                515                 520                 525

Leu Leu Asp Ala Ala Gly Val Ala Pro Leu Leu Thr Thr Ala Glu Ala
                530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Met Phe
                565                 570

<210> SEQ ID NO 8
<211> LENGTH: 573
<212> TYPE: PRT
<213> ORGANISM: Homo sapiens

<400> SEQUENCE: 8

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
                20                  25                  30

Gly Ala Asp Ala Arg Ala Leu Met Leu Gln Gly Val Asp Leu Leu Ala
                35                  40                  45

Asp Ala Val Ala Val Thr Met Gly Pro Lys Gly Arg Thr Val Ile Ile
                50                  55                  60

Glu Gln Ser Trp Gly Ser Pro Lys Val Thr Lys Asp Gly Val Thr Val
65              70                  75                  80
```

```
Ala Lys Ser Ile Asp Leu Lys Asp Lys Tyr Lys Asn Ile Gly Ala Lys
                85                  90                  95
Leu Val Gln Asp Val Ala Asn Asn Thr Asn Glu Glu Ala Gly Asp Gly
            100                 105                 110
Thr Thr Thr Ala Thr Val Leu Ala Arg Ser Ile Ala Lys Glu Gly Phe
            115                 120                 125
Glu Lys Ile Ser Lys Gly Ala Asn Pro Val Glu Ile Arg Arg Gly Val
            130                 135                 140
Met Leu Ala Val Asp Ala Val Ile Ala Glu Leu Lys Lys Gln Ser Lys
145                 150                 155                 160
Pro Val Thr Thr Pro Glu Glu Ile Ala Gln Val Ala Thr Ile Ser Ala
                165                 170                 175
Asn Gly Asp Lys Glu Ile Gly Asn Ile Ile Ser Asp Ala Met Lys Lys
            180                 185                 190
Val Gly Arg Lys Gly Val Ile Thr Val Lys Asp Gly Lys Thr Leu Asn
            195                 200                 205
Asp Glu Leu Glu Ile Ile Glu Gly Met Lys Phe Asp Arg Gly Tyr Ile
            210                 215                 220
Ser Pro Tyr Phe Ile Asn Thr Ser Lys Gly Gln Lys Cys Glu Phe Gln
225                 230                 235                 240
Asp Ala Tyr Val Leu Leu Ser Glu Lys Lys Ile Ser Ser Ile Gln Ser
                245                 250                 255
Ile Val Pro Ala Leu Glu Ile Ala Asn Ala His Arg Lys Pro Leu Val
            260                 265                 270
Ile Ile Ala Glu Asp Val Asp Gly Glu Ala Leu Ser Thr Leu Val Leu
            275                 280                 285
Asn Arg Leu Lys Val Gly Leu Gln Val Val Ala Val Lys Ala Pro Gly
            290                 295                 300
Phe Gly Asp Asn Arg Lys Asn Gln Leu Lys Asp Met Ala Ile Ala Thr
305                 310                 315                 320
Gly Gly Ala Val Phe Gly Glu Glu Gly Leu Thr Leu Asn Leu Glu Asp
                325                 330                 335
Val Gln Pro His Asp Leu Gly Lys Val Gly Glu Val Ile Val Thr Lys
            340                 345                 350
Asp Asp Ala Met Leu Leu Lys Gly Lys Gly Asp Lys Ala Gln Ile Glu
            355                 360                 365
Lys Arg Ile Gln Glu Ile Ile Glu Gln Leu Asp Val Thr Thr Ser Glu
            370                 375                 380
Tyr Glu Lys Glu Lys Leu Asn Glu Arg Leu Ala Lys Leu Ser Asp Gly
385                 390                 395                 400
Val Ala Val Leu Lys Val Gly Gly Thr Ser Asp Val Glu Val Asn Glu
                405                 410                 415
Lys Lys Asp Arg Val Thr Asp Ala Leu Asn Ala Thr Arg Ala Ala Val
            420                 425                 430
Glu Glu Gly Ile Val Leu Gly Gly Gly Cys Ala Leu Leu Arg Cys Ile
            435                 440                 445
Pro Ala Leu Asp Ser Leu Thr Pro Ala Asn Glu Asp Gln Lys Ile Gly
            450                 455                 460
Ile Glu Ile Ile Lys Arg Thr Leu Lys Ile Pro Ala Met Thr Ile Ala
465                 470                 475                 480
Lys Asn Ala Gly Val Glu Gly Ser Leu Ile Val Glu Lys Ile Met Gln
                485                 490                 495
Ser Ser Ser Glu Val Gly Tyr Asp Ala Met Ala Gly Asp Phe Val Asn
            500                 505                 510
```

```
Met Val Glu Lys Gly Ile Ile Asp Pro Thr Lys Val Val Arg Thr Ala
        515                 520                 525

Leu Leu Asp Ala Ala Gly Val Ala Ser Leu Leu Thr Thr Ala Glu Ala
    530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Met Phe
                565                 570

<210> SEQ ID NO 9
<211> LENGTH: 10
<212> TYPE: PRT
<213> ORGANISM: artificial sequence
<220> FEATURE:
<223> OTHER INFORMATION: pROTECTIVE COMMON MOTIF
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 9

Val Xaa Xaa Glu Xaa Xaa Trp Gly Xaa Pro
1               5                   10

<210> SEQ ID NO 10
<211> LENGTH: 16
<212> TYPE: PRT
<213> ORGANISM: Mycobacterium tuberculosis

<400> SEQUENCE: 10

Lys Ala Val Glu Lys Val Thr Glu Thr Leu Leu Lys Gly Ala Lys Glu
1               5                   10                  15

<210> SEQ ID NO 11
<211> LENGTH: 16
<212> TYPE: PRT
<213> ORGANISM: Mycobacterium tuberculosis

<400> SEQUENCE: 11

Phe Gly Leu Gln Leu Glu Leu Thr Glu Gly Met Arg Phe Asp Lys Gly
1               5                   10                  15

<210> SEQ ID NO 12
<211> LENGTH: 16
<212> TYPE: PRT
<213> ORGANISM: Mycobacterium tuberculosis

<400> SEQUENCE: 12

Ala Val Leu Glu Asp Pro Tyr Ile Leu Leu Val Ser Ser Lys Val Ser
1               5                   10                  15

<210> SEQ ID NO 13
<211> LENGTH: 16
<212> TYPE: PRT
<213> ORGANISM: Mycobacterium tuberculosis

<400> SEQUENCE: 13

Leu Glu Lys Val Ile Gly Ala Gly Lys Pro Leu Leu Ile Ile Ala Glu
```

<210> SEQ ID NO 14
<211> LENGTH: 16
<212> TYPE: PRT
<213> ORGANISM: Mycobacterium tuberculosis

<400> SEQUENCE: 14

Ile Arg Gly Thr Phe Lys Ser Val Ala Val Lys Ala Pro Gly Phe Gly
1               5                   10                  15

<210> SEQ ID NO 15
<211> LENGTH: 16
<212> TYPE: PRT
<213> ORGANISM: Mycobacterium tuberculosis

<400> SEQUENCE: 15

Gln Glu Ile Glu Asn Ser Asp Ser Asp Tyr Asp Arg Glu Lys Leu Gln
1               5                   10                  15

<210> SEQ ID NO 16
<211> LENGTH: 16
<212> TYPE: PRT
<213> ORGANISM: Mycobacterium tuberculosis

<400> SEQUENCE: 16

Gly Val Ala Val Ile Lys Ala Gly Ala Ala Thr Glu Val Glu Leu Lys
1               5                   10                  15

<210> SEQ ID NO 17
<211> LENGTH: 16
<212> TYPE: PRT
<213> ORGANISM: Mycobacterium tuberculosis

<400> SEQUENCE: 17

Ser Ala Leu Gln Asn Ala Ala Ser Ile Ala Gly Leu Phe Leu Thr Thr
1               5                   10                  15

<210> SEQ ID NO 18
<211> LENGTH: 13
<212> TYPE: PRT
<213> ORGANISM: Mycobacterium tuberculosis
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 18

Gly Xaa Arg Asn Val Val Leu Glu Lys Lys Trp Xaa Gly
1               5                   10

<210> SEQ ID NO 19
<211> LENGTH: 14
<212> TYPE: PRT
<213> ORGANISM: Mycobacterium tuberculosis
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 19

```
Ala Xaa Val Glu Lys Val Thr Glu Thr Leu Leu Lys Xaa Gly
1               5                   10
```

```
<210> SEQ ID NO 20
<211> LENGTH: 13
<212> TYPE: PRT
<213> ORGANISM: Mycobacterium tuberculosis
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 20

Ala Xaa Lys Glu Val Glu Thr Lys Glu Gln Ile Xaa Ala
1               5                   10
```

```
<210> SEQ ID NO 21
<211> LENGTH: 15
<212> TYPE: PRT
<213> ORGANISM: Mycobacterium tuberculosis

<400> SEQUENCE: 21

Arg Lys Val Val Val Thr Lys Asp Ala Glu Thr Thr Ile Val Glu
1               5                   10                  15
```

```
<210> SEQ ID NO 22
<211> LENGTH: 15
<212> TYPE: PRT
<213> ORGANISM: Mycobacterium tuberculosis
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 22

Ser Xaa Asp Tyr Asp Arg Glu Lys Leu Gln Glu Arg Leu Xaa Ala
1               5                   10                  15
```

```
<210> SEQ ID NO 23
<211> LENGTH: 18
<212> TYPE: PRT
<213> ORGANISM: Mycobacterium tuberculosis
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 23

Ala Xaa Thr Glu Val Glu Leu Lys Glu Arg Lys His Arg Ile Glu Asp
1               5                   10                  15

Xaa Ala
```

```
<210> SEQ ID NO 24
<211> LENGTH: 17
<212> TYPE: PRT
<213> ORGANISM: Mycobacterium tuberculosis
<220> FEATURE:
```

-continued

```
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 24

Gly Xaa Leu Gln Leu Glu Leu Thr Glu Gly Met Arg Phe Asp Lys Xaa
1               5                   10                  15

Gly

<210> SEQ ID NO 25
<211> LENGTH: 16
<212> TYPE: PRT
<213> ORGANISM: Mycobacterium tuberculosis
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 25

Ser Xaa Thr Leu Val Val Asn Lys Ile Arg Gly Thr Phe Lys Xaa Ser
1               5                   10                  15
```

B-CELL EPITOPE PEPTIDES OF HSP 65, NOVEL AMINO ACID SEQUENCES, DNA ENCODING THE AMINO ACID SEQUENCES OF SAID PEPTIDES, ANTIBODIES DIRECTED AGAINST SAID PEPTIDES AND DIFFERENT USES THEREOF IN THE TREATMENT OF INFLAMMATORY AND AUTOIMMUNE DISEASES

RELATED CASES

This application is a continuation-in-part of application Ser. No. 10/931,944, filed Aug. 31, 2004, now U.S. Pat. No. 7,488,476 which is a continuation-in-part of application Ser. No. 10/853,567, filed May 24, 2004, now U.S. Pat. No. 7,247,305, which is a continuation of application Ser. No. 09/847,637, filed May 2, 2001, now U.S. Pat. No. 6,770,281 B2, which is a continuation-in-part of Intl. application Ser. No. PCT/IL99/00595, filed Nov. 4, 1999, claiming priority of Provisional. application No. 60/107,213, filed Nov. 5, 1998, the contents of all named related cases being here incorporated by reference in their entirety.

FIELD OF THE INVENTION

The present invention relates to various peptides, homologous to regions of heat shock protein (HSP), to DNA sequences encoding such peptides, DNA constructs comprising the DNA sequences, to antibodies directed against the peptides of the invention and to compositions and methods for the treatment of immune-related disorders using the peptides and antibodies of the invention.

BACKGROUND OF THE INVENTION

Throughout this application, various publications are referred to. These publications are incorporated herein in their entireties and constitute part of the description.

Arthritis is a group of conditions involving damage to the joints of the body and is the leading cause of disability in people older than fifty-five years. The term comes from the Greek 'arthros', meaning joint, and 'itis', meaning inflammation.

There are different forms of arthritis that may be generally grouped into two main categories, inflammatory arthritis, and degenerative arthritis, each has a different causes. One critical assessment of patients involves therefore differentiating inflammatory arthritis from a degenerative process, particularly, since the treatment approaches are completely different.

Inflammatory arthritis is characterized by synovitis, bone erosions, osteopenia, soft-tissue swelling, and uniform joint space narrowing. Degenerative or mechanical arthritis, known generally as osteoarthritis, are group of conditions characterized by cartilage damage. More specifically, in addition to lack of the findings described for inflammatory joint disease, degenerative findings include osteophyte formation and bone sclerosis.

Inflammatory arthritis may be further divided into several subgroups. Involvement of a single joint is indicative of either gout or a septic arthritis caused by joint infection, usually, staphylococcal, streptococcal or gonococcal infection. A systemic arthritis, in contrast, is characterized by involvement of multiple joints, and includes two main categories, rheumatoid arthritis and seronegative spondyloarthropathy.

Rheumatoid arthritis is most common in women aged 30-60 years. Serologic markers such as rheumatoid factor and antibodies to cyclic citrullinated peptide are important indicators of rheumatoid arthritis. The radiographic features of rheumatoid arthritis are those of joint inflammation and include particular osteopenia, uniform joint space loss, bone erosions, and soft-tissue swelling. Because of the chronic nature of the inflammation, additional findings such as joint subluxation and subchondral cysts may also be evident.

The seronegative spondyloarthropathy category includes psoriatic arthritis, reactive arthritis, and ankylosing Spondylitis, and is characterized by signs of joint inflammation, multiple joint involvement, and distal involvement in the hands and feet with added features of synovial proliferation. These features accompany the specific features of these arthritic diseases i.e. Psoriatic skin diseases in psoriasis, recent infection in reactive arthritis and spinal and sacroiliac involvement in ankylosing spodylitis.

Adjuvant Arthritis (AA) is a well established experimental model of inflammatory and autoimmune arthritis which can be induced in susceptible strains of rats such as inbred Lewis or Wistar strains upon vaccination with heat-killed *Mycobacterium Tuberculosis* (MT) in complete Freund's Adjuvant (CFA) [Pearson, C.M., Proc. Soc. Exp. Biol. Med. 91:95-101 (1956); Pearson, C.M. & Wood, F.D., Arthritis Rheum. 2:440 (1959); Waksman, B.H. and Wennersten, C., Int. Arch. Allergy 23:129 (1963)]. The disease cannot be induced in resistant strains of rats (e.g., Brown-Norway; Fisher [Hogervorst, E.J.M., et al. Eur. J. Immunol. 21:1289-1296 (1991); Griffiths, M.M., et al., Arthritis Rheum. 36:254 (1993)], and Lewis rats develop resistance to re-induction of the disease after recovery from arthritis.

Heat shock proteins are a family of highly conserved proteins. There is ~50% amino acid identity between the Mycobacterial HSP 65 and the mammalian mammalian HSP 60 [Jindal, S., et al., Mol. Cell. Biol. 9:2279-2283 (1989)]. The role of the 65KD heat shock protein (HSP 65) of MT in the pathogenesis of autoimmune arthritis, both in experimental animals [Van Eden, W., et al., Nature (Lond.) 331:171-173 (1988); Holoshitz, J., et al., Science (Wash. DC) 219:56-58 (1983)] as well as in humans [Holoshitz, J., et al., Lancet 2:305-309 (1986); Res, P.C.M., et al., Lancet 2:478-480 (1988); Gaston, J.S.H., et al., J. Immunol. 143:2494-2500 (1989)], has been investigated intensively in the past several years. For example, Barker et al. [Barker et al., Autoimmunity 14:73-77 (1992)] describe the suppression of arthritogenic immune responses in mice given HSP 65 and pristane. The antigen used to elicit the response was full-length HSP 65, and no attempt was made to investigate the effect of specific sub-domains or peptides deriving from this protein.

Resistance to adjuvant arthritis can be conferred by several factors: genetic background (e.g. Black-Norway or Fisher strains), old age, previous disease and pre-immunization of susceptible rats with mycobacterial HSP65. Evidence has been reported that protection from disease may be due to cellular responses to HSP65 [Hogervorst (1991) ibid.; Thole, J. et al. Infect. Immun. 55:1466-1475 (1987); Lider, O. et al. Proc. Natl. Acad. Sci. 84:4577-4580 (1987); Billingham, M. et al. J. Exp. Med. 171:339-344 (1990); Moudgil, K. et al. J. Exp. Med. 185:1307-1316 (1997)] suggesting that this protein contains different epitopes which participate in both pathogenesis and acquisition of resistance. The inventors have previously shown that resistance to AA can be transferred to a susceptible strain of rats by intravenous infusion of immunoglobulins from resistant strains, and that resistance is associated with the presence of antibodies against the 65KD MT heat shock protein (HSP 65) [Ulmansky, R., and Y. Naparstek, Eur. J. Immunol. 25:952-957 (1995)].

The present invention now illustrate the fine epitope specificity of the anti-HSP antibodies of arthritis—susceptible and resistant rats. As shown by the invention, naive Lewis rats lack antibodies to certain epitopes of the mycobacterial HSP 65 which are found naturally in young BN and old naive Lewis rats, and that are acquired by young Lewis rats after recovery from the disease. Analysis of the primary and tertiary structure of the whole MT HSP 65KD molecule indicated that these "protective" epitopes are potential B-cell epitopes with a non-conserved amino acid sequences that are found on the outer surface of the molecule.

Pre-immunization of Lewis rats with one of the "protective" epitopes prior to induction of the disease induced antibodies against the whole molecule as well as resistance to disease induction. This sixteen amino acid peptide, termed peptide-6 (also denoted by SEQ ID: NO. 2) corresponds also to the self-HSP 60 epitope to which antibodies were found in the arthritis resistant rats, but not in the arthritis-susceptible naive Lewis rats.

The present invention therefore provides a working hypothesis centered on the failure of the immune system of RA susceptible patients to produce an antibody against this B-cell epitope peptide-6. The invention further shows that antibodies directed against peptide-6 interact not only with peptide-6, but moreover, they cross react directly with a surface ligand on macrophages, and this interaction is the key to the mechanism of action of these antibodies. Following binding of the anti-peptide-6 antibodies to macrophages, there is activation of a signal transduction pathway that leads to an increase in production and secretion of cytokines, specifically IL-10 that as an anti-inflammatory cytokine, attenuates and inhibits an inflammatory process, thereby leading to amelioration and treatment of an inflammatory disorder. This tilts the balance between pro-inflammatory Th1 cytokines, such as tumor necrosis factor alpha (TNF-alpha), and anti-inflammatory Th2 cytokines, such as IL-10. Modulation of the Th1/Th2 balance towards a Th2 anti-inflammatory response by the antibodies of the invention may be therefore applied for treating inflammatory disorders. The results disclosed by the present invention clearly establish the feasibility of using the B-cell epitope peptides of the invention and particularly the use of antibodies directed against such peptides as immunomodulators, specifically for modulating the Th1/Th2 balance towards a Th2 anti-inflammatory response.

Therefore, one object of the invention is to provide peptides, specifically peptides having the amino acid sequence of any one of SEQ ID NO. 1, 2, 3, and 4, antibodies directed against said peptides as well as compositions comprising the same for the treatment of immune-related disorders, particularly, inflammatory and autoimmune disorders.

Another object of the invention is to provide methods and compositions for enhancing the expression of IL-10 in a subject in need thereof.

These and other objects of the invention will become apparent as the description proceeds.

SUMMARY OF THE INVENTION

In a first aspect, the invention relates to a composition comprising as an active ingredient an effective amount of at least one isolated and purified antibody directed against a peptide consisting of the amino acid sequence of SEQ ID: NO. 1 or against biologically functional homologues and derivatives thereof. According to one embodiment, the biologically functional homologues and derivatives of the peptide of SEQ ID NO. 1 may be selected from the group consisting of SEQ ID: NO. 2 and SEQ ID: NO. 3. It should be therefore appreciated that the composition of the invention may comprise any of the antibodies of the invention, specifically, any one of the antibodies directed against the peptides of SEQ ID NO. 1, 2 or 3, or any combinations or mixtures of any of these antibodies. The composition of the invention further comprises a pharmaceutically acceptable carrier, excipient or diluent.

In another aspect, the present invention provides a pharmaceutical composition for the treatment or amelioration of an immune-related disorder. The therapeutic composition of the invention comprises as an active ingredient a therapeutically effective amount of at least one isolated and purified antibody according to the invention. More specifically, the therapeutic composition of the invention may comprise as an active ingredient any of the antibodies directed against the peptides of SEQ ID NO. 1, 2 or 3, or any combinations or mixtures of said antibodies. It should be noted that the composition of the invention may optionally further comprises a pharmaceutically acceptable carrier, excipient or diluent.

The invention further provides a composition for increasing the expression and levels of IL-10 (Interleukine-10). According to this aspect, the composition of the invention comprises as an active ingredient an effective amount of at least one of any of the isolated and purified antibodies of the invention, specifically, any one of the antibodies directed against the peptides of SEQ ID NO. 1, 2 or 3, or any combinations or mixtures of said antibodies.

According to one embodiment, the composition of the invention may be used for increasing the expression and levels of IL-10 in a subject in need thereof, thereby modulating the Th1/Th2 cell balance towards an anti-inflammatory Th2 response in the treated subject. According to one specific embodiment, such subject may be a subject suffering of an immune-related disorder.

According to another aspect, the invention relates to a method for the treatment or amelioration of an immune-related disorder. The method of the invention comprises the step of administering to a subject in need thereof a therapeutically effective amount of at least one of the isolated and purified antibodies of the invention or of a composition comprising the same.

In another aspect, the invention provides a method for increasing the expression and levels of IL-10 in a subject in need thereof. The method of the invention comprises the step of administering to the treated subject a therapeutically effective amount of at least one of any of the isolated and purified antibodies of the invention, any combinations thereof, or a composition comprising the same. It should be noted that any increase in the expression and/or levels of IL-10 may lead to modulation of the Th1/Th2 cell balance towards an anti-inflammatory Th2 response in the treated subject. Such subject may be specifically a subject suffering of an immune-related disorder.

According to a further aspect, the invention relates to a purified B cell epitope peptide consisting of the amino acid sequence of SEQ ID: NO, 1 or biologically functional homologues and derivatives thereof selected from the group consisting of SEQ ID: NO. 2 and SEQ ID: NO. 3. According to this aspect, the peptides of the invention are specifically suitable for the treatment and amelioration of an immune-related disorder.

The invention further provides a pharmaceutical composition comprising any of the peptides of the invention, for the treatment or amelioration of an immune-related disorder.

In yet another aspect, the invention provides a method for the treatment or amelioration of an immune-related disorder comprising the step of administering to a subject in need thereof a therapeutically effective amount of at least one of any of the isolated and purified peptide of the invention, or any combinations and mixtures thereof, or of a composition comprising the same.

DESCRIPTION OF THE FIGURES

FIG. 1 Amino acid comparison of three HSP 60 sequences

*Mycobacterium Tuberculosis*, rat HSP 60 and human HSP 60 (reference sequences PO6806, P19227 and P10809, corresponding to SEQ ID: NOs. 6, 7 and 8 respectively), were compared with pileup program from GCG-Wisconsin Package v9.0. The conserved regions are indicated (consensus). Bold, underlined residues represent the preferred peptides.

Figure 2:
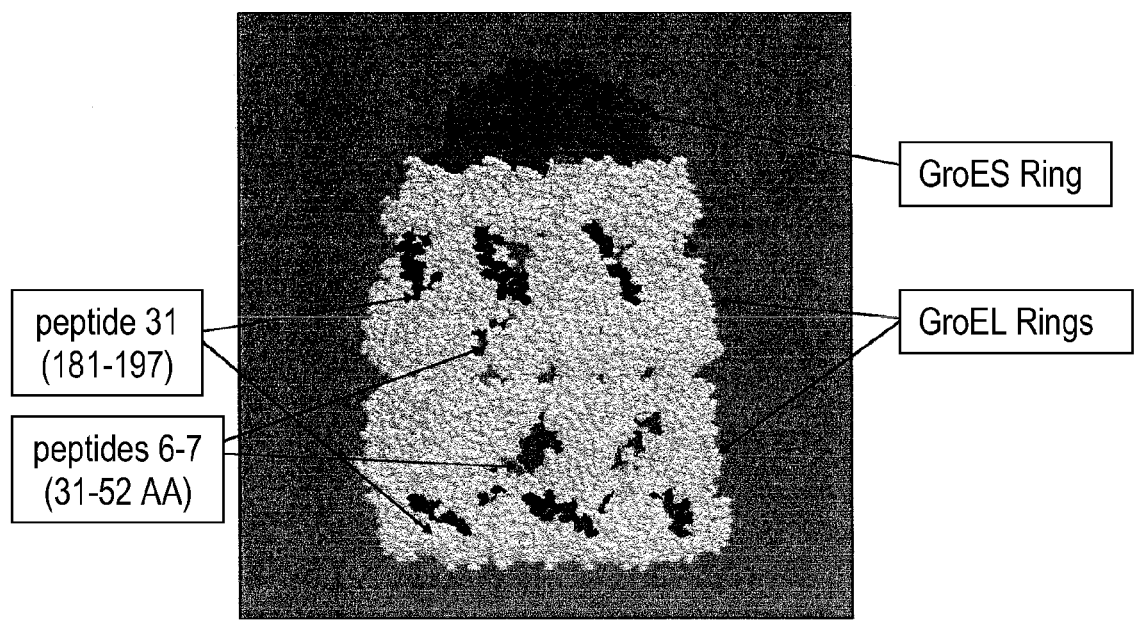

FIG. 2 Three dimensional structure of the *E. coli* GroEL-GroES complex

The GroES heptameric ring is shown in dark gray. The two GroEL heptameric rings are shown in light gray. Peptides 6-7 (amino acids 31-52) and 31 (amino acids 181-197) are also indicated.

Figure 3A:
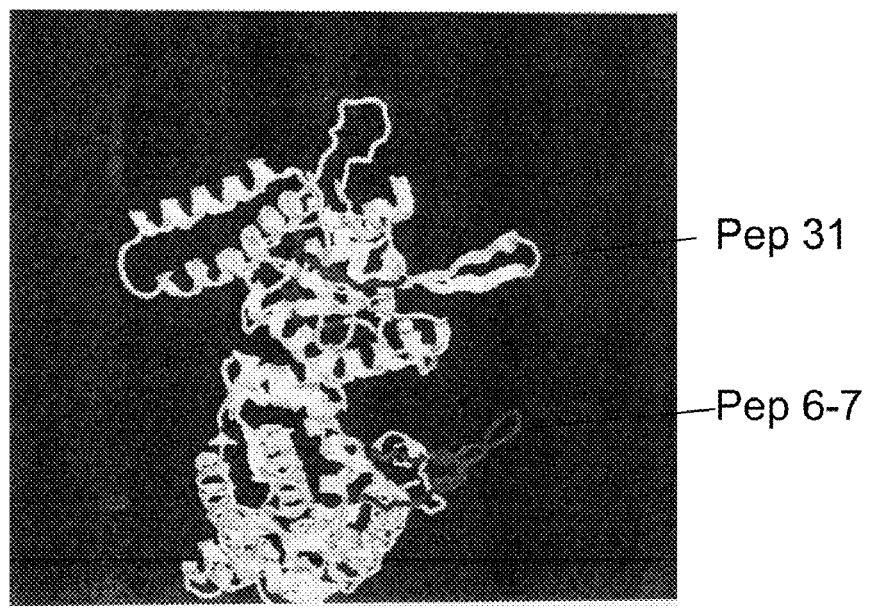
Figure 3B:
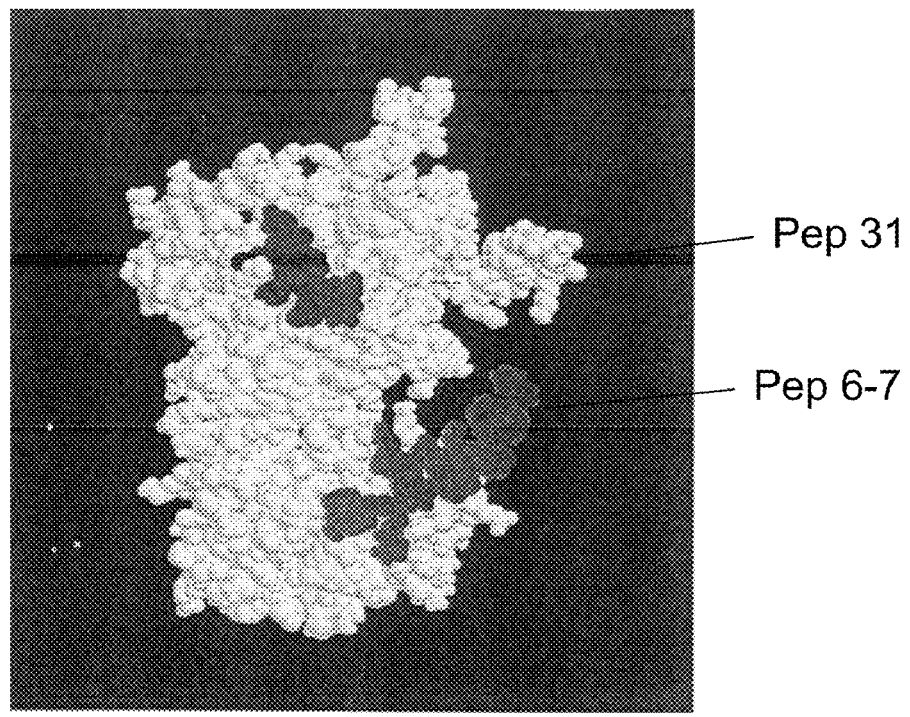

FIGS. 3A-3B The location of peptides 6, 7 and 31 in the HSP 65 monomer

The location of peptides 6, 7 and 31 in the HSP 65 monomer is indicated in a secondary structure configuration (FIG. 3A) and in the space filling mode (FIG. 3B).

Figure 4:
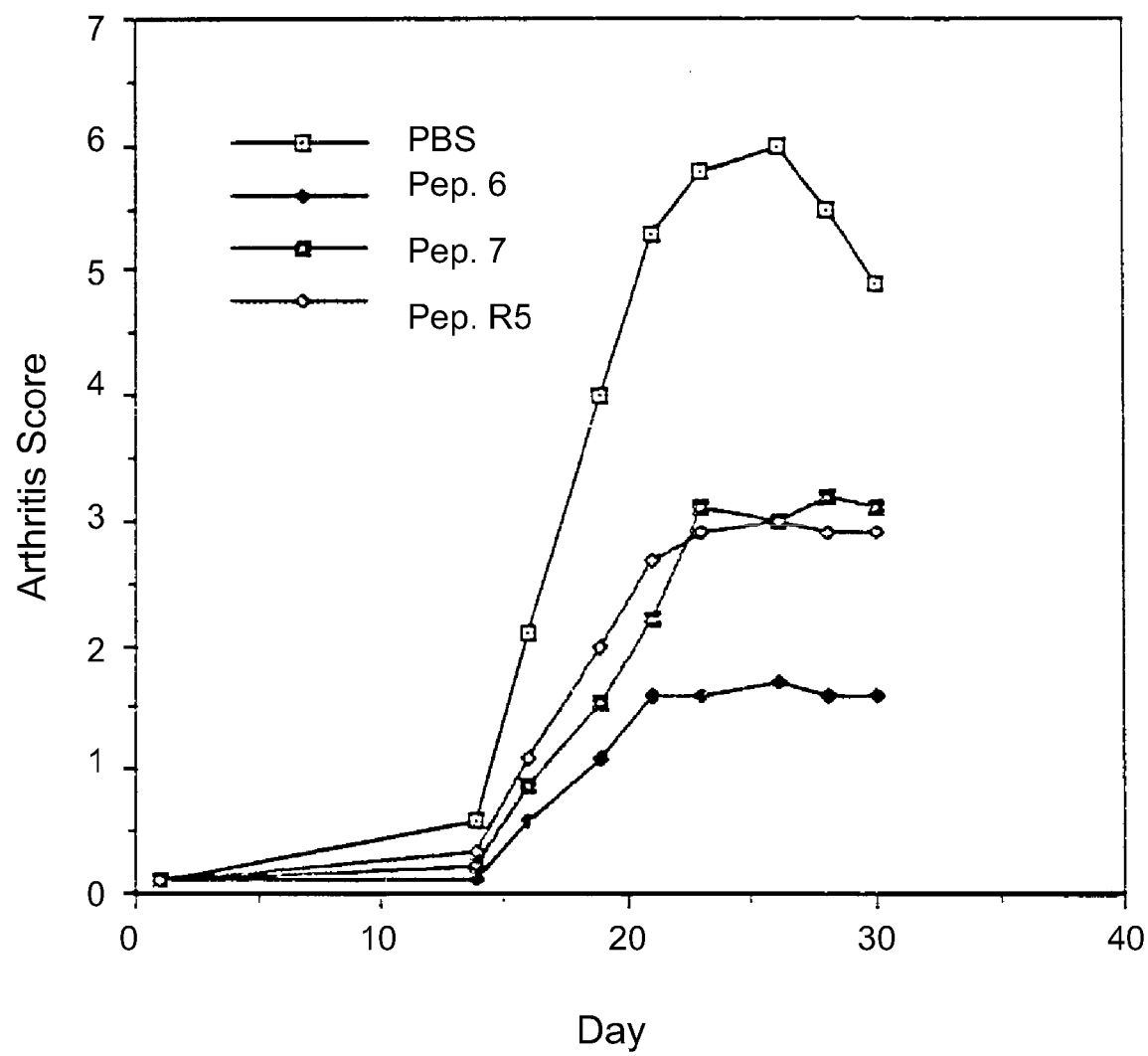

FIG. 4 AA development in Lewis rats after vaccination with HSP peptides

Measurement of AA disease score in Lewis rat immunized with HSP peptides 6, 7 and R5 prior to AA induction. PBS was used as control.

FIG. 5 The protecting motif within peptides 6, 7 and R5

A common motif within peptides 6, 7 and R5, V-E-WG-P (also denoted by SEQ ID NO: 9), is shown.

Figure 6:
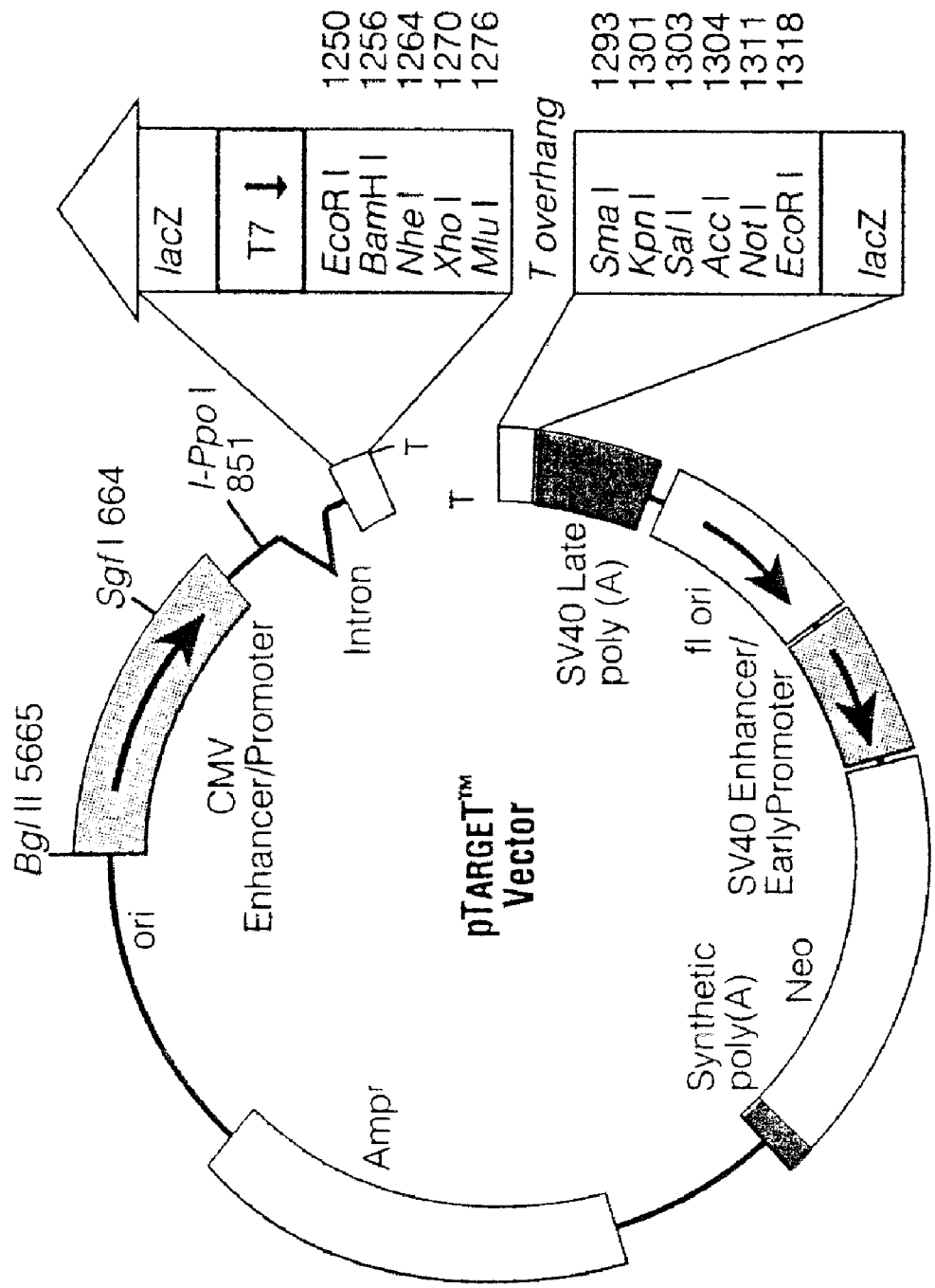

FIG. 6 pTARGET plasmid map

Description map of the PTARGET plasmid is shown.

Figure 7:
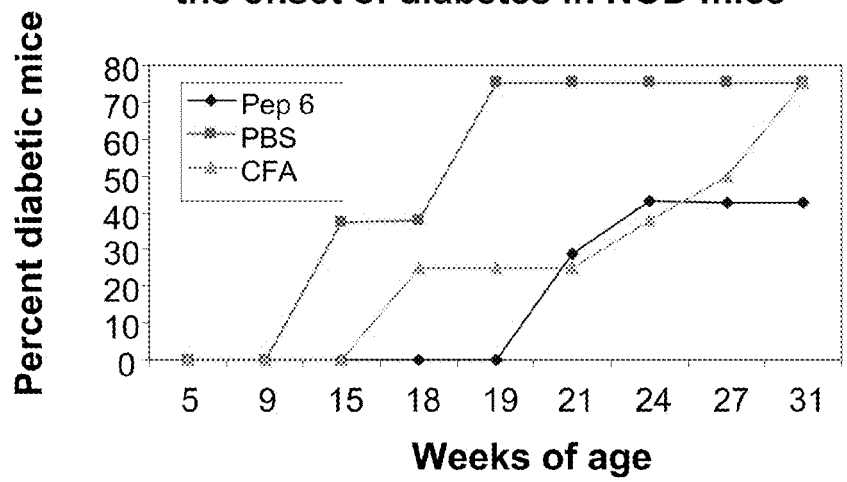

FIG. 7 Effect of peptide 6 immunization on the onset of diabetes in NOD mice Naive NOD mice were immunized 3 times intradermally (I.D.) with 100 μg peptide 6 (SEQ ID: NO. 2) in CFA and IFA. Control mice received PBS. Mice were monitored for the onset of diabetes by glucose test and for anti-peptide 6 or anti-HSP 65 antibodies by ELISA. Mice immunized with the peptide developed anti-peptide 6 as well as anti-HSP 65 antibodies as detected by OD (1.52±0.07 and 1.43±0.13 respectively) in comparison to CFA immunized mice (0.05±0.01 and 0.01±0.01) and control mice (0.09±0.06 and 0.16±0.16).

Figure 8:
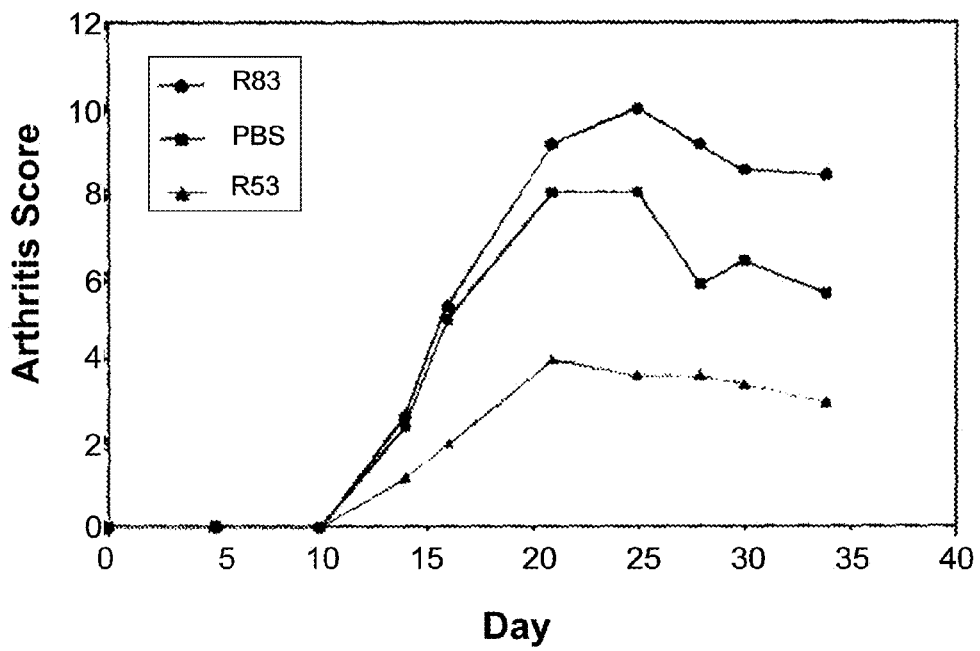

FIG. 8 Modulation of AA by rat anti-peptide 6 monoclonal antibody R53F

Lewis rats were immunized with MT in CFA and treated with the monoclonal rat anti-peptide 6 R53F immunoglobulin, a control rat monoclonal antibody R83D or PBS. Two injections were given, the first intravenously (I.V.) and the second intraperitoneally (I.P.). Disease severity was evaluated every other day. Arthritis score expresses the mean result of 5 animals. *p<0.05 compared to PBS treated rats.

Figure 9:
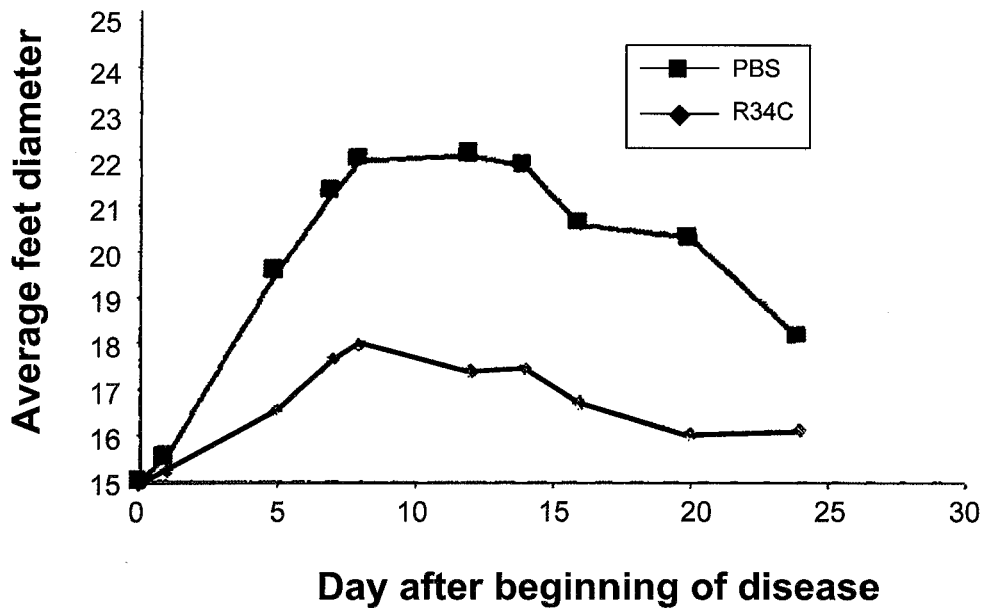

FIG. 9 Modulation of Collagen arthritis by rat anti-peptide 6 monoclonal antibody R34C Collagen arthritis was induced in DBA/1 mice. Mice were then treated with either rat anti-peptide 6 monoclonal antibody R34C or PBS. Arthritis was evaluated by measuring feet diameter.

Figure 10:
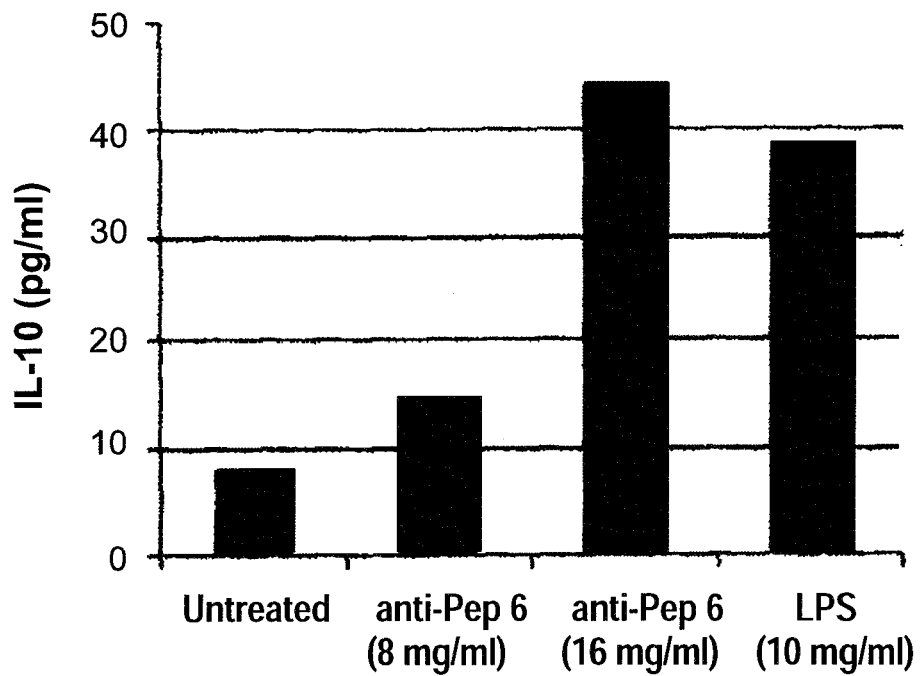

FIG. 10 Induction of IL-10 secretion in macrophages incubated with rat anti-peptide 6 R53F monoclonal antibody Naive human macrophages were incubated (24 h, 37° C., 5% $CO_2$) in RPMI with LPS (10 ng/ml) or with the rat monoclonal anti peptide 6 R53F antibody (8 and 16 μg/ml). Untreated cells served as control. IL-10 secretion to the medium was measured by ELISA.

Figure 11:
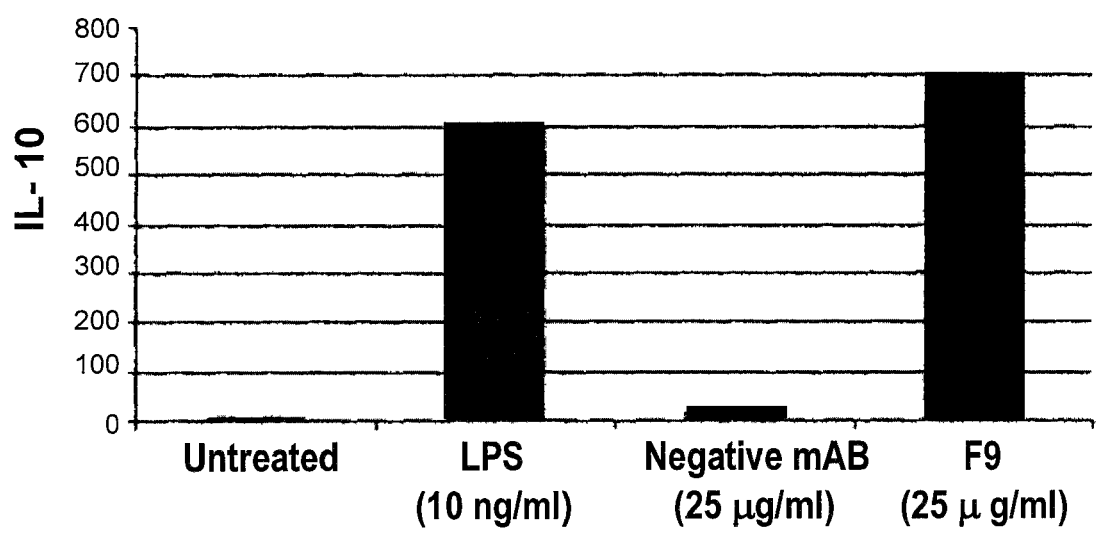

FIG. 11 Induction of IL-10 secretion in macrophages incubated with mouse anti-peptide 6 MF9 monoclonal antibody Naive human macrophages were incubated in RPMI with LPS (10 ng/ml), the mouse monoclonal anti peptide 6 MF9 antibody (25 μg/ml) or with mouse unrelated monoclonal antibody (25 μg/ml). Untreated cells served as control. IL-10 secretion (pg/ml) to the medium was measured by ELISA.

Figure 12A:
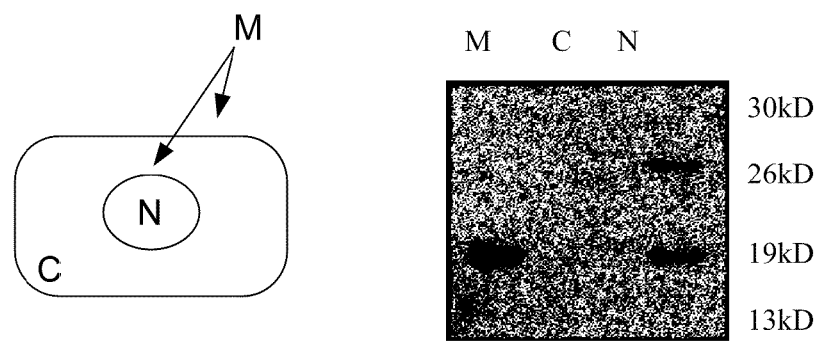
Figure 12B:
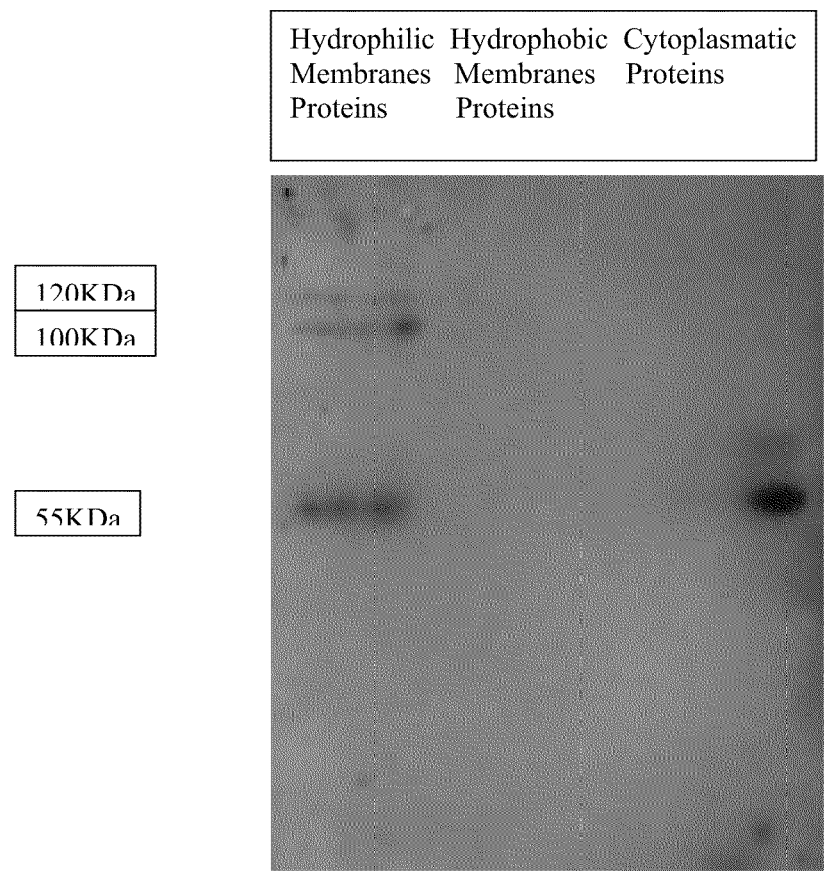

FIG. 12A-12B Binding of rat anti-peptide 6 antibodies to human macrophages cell extract FIG. 12A: Human macrophages were fractionated to nuclear, cytoplasmic and membrane fractions. The fractions were resolved by SDS-PAGE and subjected to Western blotting using the monoclonal rat anti-peptide 6 R34C (10 μg/ml) antibody. The monoclonal antibody bound to 19KD and 30KD nuclear bands and to a 19KD membrane band. Control polyclonal rat antibodies (10 μg/ml) did not bind to these bands (not shown).

FIG. 12B: Human macrophages purified from human peripheral blood were fractionated to Hydrophilic membrane, Hydrophobic membrane and Cytoplasmic proteins Ten micrograms (μg) of each macrophage protein fraction were resolved by 9% SDS-PAGE under denaturing conditions and subjected to Western blot analysis using 10 μg/ml rat monoclonal anti-peptide 6 antibody (clone B-24). B-24 monoclonal antibody showed a 120KD, a 100KD and a 55KD bands in the Hydrophilic membrane fraction and a 55KD band in the Cytoplasmic fraction. Control polyclonal rat antibodies (10 μg/ml) did not bind to these bands (not shown).

Figure 13:
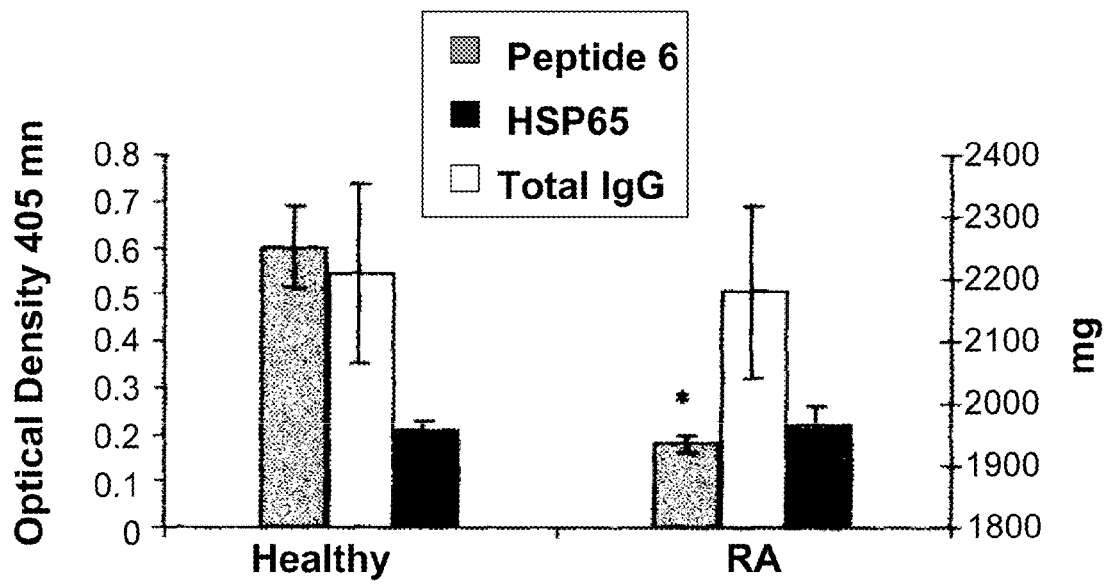

FIG. 13 Antibodies to peptide 6 and to HSP 65 in RA patients and healthy donors Sera from healthy donors (n=17) or rheumatoid arthritis (RA) patients (n=25) were tested for antibody binding to peptide 6 and HSP 65 by ELISA and for immunoglobulin G levels. Anti-peptide 6 antibodies were found to be significantly lower in the RA patients (*p<0.01).

Figure 14:
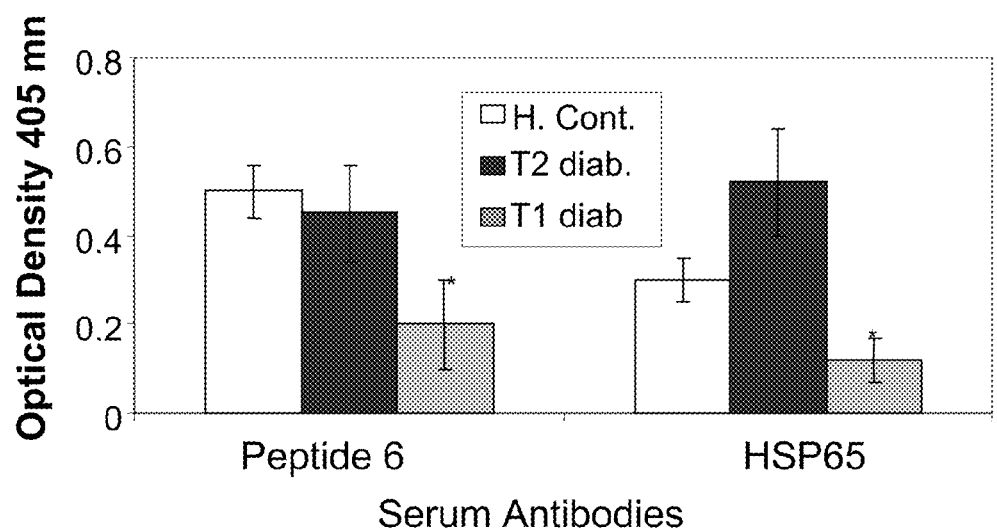

FIG. 14 Antibodies to peptide 6 and to HSP 65 in Diabetic patients and healthy donors Sera from healthy donors (n=11), type 1 diabetes patients (n=10) and type 2 diabetes patients (n=10) were tested for antibody binding to peptide 6 and HSP 65 by ELISA. Anti-peptide 6 antibodies were found to be significantly lower in type 1 diabetes patients (*p<0.05) compared to type 2 diabetes patients and healthy controls.

DETAILED DESCRIPTION OF THE INVENTION

As shown by the present invention, resistance to AA can also be conferred by antibodies against HSP65 and can be passively transferred by intravenous infusion of immunoglobulins from arthritis-resistant strains to arthritis-susceptible rats. Further analysis defined the epitope specificity of the anti-HSP protective antibodies to amino-acid residues 31-46, designated as peptide-6 (also denoted by SEQ ID NO. 2). Vaccination of Lewis rats with this peptide resulted in the production of antibodies against the whole molecule as well as resistance to disease induction. Protective antibodies were absent in arthritis-susceptible, young Lewis rats but present in resistant animals such as BN, old naive Lewis and young Lewis rats after recovery from AA. Moreover, using there different animal models, specifically, the arthritis AA and CIA models and the diabetic NOD mice models, these antibodies were shown as exhibiting beneficial effect on inflammatory diseases such as inflammatory arthritis and autoimmune condition for example, diabetes. The invention further shows that antibodies directed against peptide-6 interact not only with peptide-6, but moreover, they cross react directly with a surface ligand on macrophages, and this interaction is the key to the mechanism of action of these antibodies. Following binding of the anti-peptide-6 antibodies to macrophages, there is activation of a signal transduction pathway that leads to an increase in production and secretion of the anti-inflammatory cytokine, IL-10. In addition, these results clearly demonstrate the feasibility of using the peptides of the invention as well as the antibodies of the invention as a new therapeutic approach for treating immune-related disorders.

Thus, according to a first aspect, the invention relates to a composition comprising as an active ingredient an effective amount of at least one isolated and purified antibody directed against a peptide consisting of the amino acid sequence of SEQ ID. NO. 1 or against biologically functional homologues and derivatives thereof. According to one embodiment, the biologically functional homologues and derivatives of the peptide of SEQ ID NO. 1 may be selected from the group consisting of SEQ ID. NO. 2 and SEQ ID. NO. 3. The composition of the invention further comprises a pharmaceutically acceptable carrier, excipient or diluent. It should be appreciated that the composition of the invention may comprise any of the antibodies of the invention, specifically, any one of the antibodies directed against the peptides of SEQ ID NO. 1, 2 or 3, or any combinations or mixtures of said antibodies.

According to one specific embodiment, the composition of the invention comprises as an active ingredient at least one antibody directed against a peptide consisting of the amino acid sequence of SEQ ID. NO. 1.

According to another embodiment, the composition of the invention comprises as an active ingredient at least one antibody directed against a purified peptide consisting of the amino acid sequence of SEQ ID. NO. 2.

According to another embodiment, the composition of the invention comprises as an active ingredient at least one antibody directed against a purified peptide consisting of the amino acid sequence of SEQ ID. NO. 3.

In another aspect, the present invention provides a pharmaceutical composition for the treatment and/or amelioration of an immune-related disorder. The therapeutic composition of the invention comprises as an active ingredient a therapeutically effective amount of at least one isolated and purified antibody directed against a peptide consisting of the amino acid sequence of SEQ ID. NO. 1 or against biologically functional homologues and derivatives thereof. It should be noted that the composition of the invention may optionally further comprises a pharmaceutically acceptable carrier, excipient or diluent. According to one embodiment, the biologically functional homologues and derivatives of the peptide of SEQ ID NO. 1 may be selected from the group consisting of SEQ ID. NO. 2 and SEQ ID. NO. 3.

Thus, according to a specific embodiment, the therapeutic composition of the invention may comprise as an active ingredient any of the antibodies of the invention, specifically, any one of the antibodies directed against the peptides of SEQ ID NO. 1, 2 or 3, or any combinations or mixtures of said antibodies.

According to another specific embodiment, the therapeutic composition of the invention comprises at least one antibody specifically directed against peptide-6, also indicated herein as the peptide of SEQ ID NO. 2.

It should be noted that the antibodies used by the compositions and methods of the invention are preferably isolated and purified.

The term "antibody" as used in connection with the present invention refers to both polyclonal and monoclonal antibodies. Polyclonal antibodies may be generated in rabbits, chicken, mice, rats, sheep, or similar mammals. The generation of polyclonal antibodies against peptides is described in the above-noted Current Protocols in Immunology, Wiley and Sons Inc. Chapter 9, fully incorporated herein by reference.

Monoclonal antibodies may be prepared from B cells taken from the spleen or lymph nodes of immunized animals, in particular rats or mice, by fusion with immortalized B cells under conditions which favor the growth of hybrid cells.

The technique of generating monoclonal antibodies is described in many articles and textbooks, such as the above-noted Chapter 2 of Current Protocols in Immunology. Chapter 9 therein describes the immunization of laboratory animals with peptides. Spleen or lymph node cells of these animals may be used in the same way as spleen or lymph node cells of protein-immunized animals, for the generation of monoclonal antibodies as described in Chapter 2 therein.

The term "antibody" is also meant to include intact molecules, as well as fragments thereof, such as, for example, Fv, Fab and F(ab')2, which are capable of binding antigen. Fab and F(ab')2 fragments lack the Fc fragment of intact antibody, clear more rapidly from the circulation, and may have less non-specific tissue binding than an intact antibody. An Fv fragment of an antibody is the smallest unit of the antibody that retains the binding characteristics and specificity of the whole molecule. The Fv fragment is a non-covalently associated heterodimer of the variable domains of the antibody heavy chain and light chain.

Humanized and immortal fusion cell lines that effectively and efficiently fuse with a mortal antibody producing human lymphocytes (B cells), create human hybridoma cells (hu-hybridomas) which have the antibody producing characteristics of the human lymphocytes.

The therapeutic antibodies of the invention can be antibodies produced in any mammal, for example, murine, rabbit, goat, rat etc. Alternatively, the antibodies of the invention may be chimeric antibodies (combine the specificity of the murine antibody with the efficient human immune system interaction of a human antibody); humanized antibodies (the minimum mouse part from a murine antibody is transplanted onto a human antibody); and fully human antibodies (antibodies derived from transgenic mice carrying human antibody genes or from human cells). TransChromo (TC) technology allows generating a wide variety of fully-human monoclonal antibodies using mice which carry the whole human immunoglobulin loci. Human immunoglobulin phage display libraries are also an additional source for isolation of human monoclonal antibodies to be used for therapeutic purposes.

An antibody is said to be "directed against" a molecule, for example, any of the peptides of the invention, specifically, the peptides of any one of SEQ ID NO. 1, 2 and 3, if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

Therefore, it should be appreciated that the peptides of the invention may be used as an antigen. An "antigen" is a molecule or a portion of a molecule capable of being bound by an antibody which is additionally capable of inducing an animal to produce antibody capable of binding to an epitope of that antigen. An antigen may have one or more than one epitope.

The specific reaction referred to above is meant to indicate that the antigen will react, in a highly selective manner, with its corresponding antibody and not with the multitude of other antibodies which may be evoked by other antigens.

The results presented by the present invention clearly demonstrate the therapeutic potential of the antibodies of the invention on immune-related disorders. Thus, according to another embodiment, the pharmaceutical composition of the invention may be specifically suitable for treating an immune-related disorder, for example, an autoimmune or inflammatory disorder.

As indicated above, the following Examples clearly demonstrate, using two different animal models, the applicability of the antibodies of the invention for treating inflammatory arthritis. More specifically, Lewis rats treated for AA induction and concomitantly with an anti-peptide 6 monoclonal antibody (R53F) showed a significant reduction in arthritis. Similarly, treatment of DBA/1 mice, induced to develop Collagen arthritis (CIA), with an anti-peptide 6 monoclonal antibody (R34C) reduced arthritis severity.

Furthermore, as indicated by Berent, J. et al., [Prakken B.J. et al., Springer Semin. Immunopathol. 25: 7-63 (2003)], Adjuvant arthritis (AA) is a well established animal model for Rheumatoid arthritis (RA), Juvenile idiopathic arthritis (JIA) and Septic arthritis. Moreover, different publications [Myers et al. Life Sciences 61(19): 1861-1878 (1997) and Brand et al. Springer Semin Immunopathol (2003) 25:3-18 (2003), respectively], clearly indicate that collagen induced arthritis (CIA) is also an established model for RA as well as to other autoimmunity, rheumatic diseases and inflammation.

It should be appreciated there are different forms of arthritis that may be generally grouped into two main categories, inflammatory arthritis, and degenerative arthritis, each has a different causes. Therefore, according to one specific embodiment, the pharmaceutical compositions of the invention may be specifically intended for the treatment and/or amelioration of an inflammatory disorder, for example, an inflammatory arthritis.

Inflammatory arthritis is characterized by synovitis, bone erosions, osteopenia, soft-tissue swelling, and uniform joint space narrowing. More specifically, the hallmarks of joint inflammation are synovitis and erosion of bone. The latter will initially appear as a focal discontinuity of the thin, white, subchondral bone plate. Normally, this subchondral bone plate can be seen even in cases of severe osteopenia, whereas its discontinuity indicates erosion. Although it is true that periarticular osteopenia and focal subchondral osteopenia can appear prior to true bone erosion, it is the presence of bone erosion that indicates definite joint inflammation. As the bone erosion enlarges, osseous destruction extends into the trabeculae within the medullary space. One important feature of inflammatory arthritis relates to the concept of marginal bone erosion. This term is given to bone erosion that is located at the margins of an inflamed synovial joint. This specific location represents that portion of the joint that is intraarticular but not covered by hyaline cartilage. Therefore, early joint inflammation will produce marginal erosions prior to erosions of the subehondral bone plate beneath the articular surface. When looking for bone erosions, multiple views of a joint are essential to profile the various bone surfaces. A second important characteristic of an inflammatory joint process is uniform joint space narrowing. This occurs because destruction of the articular cartilage is uniform throughout the intraarticular space. A third finding of inflammatory joint disease is soft-tissue swelling.

It should be appreciated that inflammatory arthritis may be further divided into several subgroups, and therefore, the compositions, as well as the methods of the invention (described herein after) may be applicable for treating every inflammatory arthritis condition of the different subgroups.

More specifically, involvement of a single joint is indicative of a Septic arthritis. The cause of septic arthritis is usually related to hematogenous seeding owing to staphylococcal or streptococcal microorganisms. The radiographic features of a septic joint encompass those of any inflammatory arthritis, namely, periarticular osteopenia, uniform joint space narrowing, soft-tissue swelling, and bone erosions. Not all findings may be present simultaneously, and, acutely, bone erosions may not be evident. Thus, according to one embodiment, the compositions and methods of the invention may be used for the treatment and/or amelioration of septic arthritis.

A systemic arthritis, in contrast, is characterized by involvement multiple joints, and includes two main categories, rheumatoid arthritis and seronegative spondyloarthropathy.

According to one embodiment, the compositions and methods of the invention may be used for the treatment and/or amelioration of Rheumatoid arthritis. Rheumatoid arthritis (RA) is a chronic, systemic autoimmune disorder that most commonly causes inflammation and tissue damage in joints (arthritis) and tendon sheaths, together with anemia. It can also produce diffuse inflammation in the lungs, pericardium, pleura, and the sclera of the eye, and also nodular lesions, most common in subcutaneous tissue under the skin. It can be a disabling and painful condition, which can lead to substantial loss of functioning and mobility. Serologic markers such as rheumatoid factor and antibodies to cyclic citrullinated peptide are important indicators of rheumatoid arthritis. The radiographic features of rheumatoid arthritis are those of joint inflammation and include particular osteopenia, uniform joint space loss, bone erosions, and soft-tissue swelling. Because of the chronic nature of the inflammation, additional findings such as joint subluxation and subehondral cysts may also be evident.

The seronegative spondyloarthropathy category includes psoriatic arthritis, reactive arthritis, and ankylosing Spondylitis, and is characterized by signs of inflammation, multiple joint involvement, and distal involvement in the hands and feet with added features of bone proliferation. Thus, according to one embodiment, the compositions and methods of the invention may be used for the treatment and/or amelioration of any condition of the seronegative spondyloarthropathy category.

More specifically, according to one embodiment, the compositions and methods of the invention may be used for the treatment and/or amelioration of Psoriatic arthritis. Psoriatic arthritis is a chronic disease characterized by inflammation of the skin (Psoriasis) and joints (arthritis). Nearly 306,000 people in the USA suffer from psoriatic Arthritis and additional 308,000 people are believed to suffer from the disease in the five leading markets in Europe. Psoriasis and Arthritis often appear separately. In fact, the skin disease precedes the arthritis in nearly 80% of patients. The arthritis may precede the psoriasis in up to 15% of patients.

Psoriasis, one of the characteristics of Psoriatic Arthritis, is a common skin condition that features patchy, raised, red areas of skin inflammation with scaling. Psoriasis often affects the tips of the elbows and knees, the scalp, the navel, and the area surrounding the genitals or anus. Approximately 10% of patients who have psoriasis also develop an associated inflammation of their joints. Usually, the more severe the skin symptoms are, the greater the likelihood a person will develop psoriatic arthritis. The cause of psoriatic arthritis is unknown, it may have a combination of genetic, environmental, and immune causes.

Males and females are equally likely to suffer from psoriasis. For psoriatic arthritis, males are more likely to have the spondylitic form (in which the spine is affected), and females are more likely to have the rheumatoid form (in which many joints may be involved). Psoriatic arthritis usually develops in people aged 35-55 years. However, it can develop in people of almost any age. Psoriatic arthritis shares many features with several other arthritic conditions, such as ankylosing spondylitis, reactive arthritis, and arthritis associated with Crohn's disease and ulcerative colitis. All of these conditions can cause inflammation in the spine and joints, in the eyes, skin, mouth, and various organs.

According to another embodiment, the compositions and methods of the invention may be used for the treatment and/or amelioration of Ankylosing Spondylitis. Ankylosing spondylitis (AS, previously known as Bechterew's disease, Bechterew syndrome, Marie Strümpell disease and a form of Spondyloarthritis), is usually a chronic and progressive form of arthritis, caused due to inflammation of multiple joints, characteristically the spinal facet joints and the sacroiliac joints at the base of the spine. While ankylosing spondylitis tends to affect these joints and the soft tissues around the spine, other joints may also be affected, as well as tissues surrounding the joints (entheses, where tendons and ligaments attach to bone). Ankylosing spondylitis may also involve areas of the body other than the joints, such as the eyes, heart, and lungs.

This disorder frequently results in bony ankylosis (or fusion), hence the term ankylosing, which is derived from the Greek word ankylos, meaning stiffening of a joint. Spondylos means vertebra (or spine) and refers to inflammation of one or more vertebrae.

The disease is estimated to affect approximately 0.1-0.2% of the general population. Ankylosing spondylitis primarily affects young males. Males are four to ten times more likely to have ankylosing spondylitis than females. Most people with the disease develop it at age 15-35 years, with an average age of 26 years at onset.

Although the exact cause is unknown, ankylosing spondylitis is believed to be due to the combination of a genetic influence and a triggering environmental factor. Approximately 90-95% of patients with ankylosing spondylitis have the tissue antigen Human Leukocyte Antigen B27 (HLA-B27), compared to 7% in the general population. People with ankylosing spondylitis often have a family history of the disease.

In yet another embodiment, the compositions and methods of the invention may be used for the treatment and/or amelioration of Reactive arthritis (ReA). Reactive arthritis, another type of seronegative spondyloarthropathy, is an autoimmune condition that develops in response to an infection in another part of the body. Coming into contact with bacteria and developing an infection can trigger reactive arthritis. It has symptoms similar to various other conditions collectively known as "arthritis," such as rheumatism. It is caused by another infection and is thus "reactive", i.e., dependent on the other condition. The "trigger" infection has often been cured or is in remission in chronic cases, thus making determination of the initial cause difficult.

The symptoms of reactive arthritis very often include a combination of three seemingly unlinked symptoms, an inflammatory arthritis of large joints, inflammation of the eyes (conjunctivitis and uveitis), and urethritis. It should be indicated that ReA is also known as Reiter's syndrome, after German physician Hans Reiter, it is also known as arthritis urethritica, venereal arthritis and polyarteritis enterica.

It should be appreciated that there are many other forms of inflammatory arthritis, including Juvenile idiopathic arthritis, gout and pseudo gout, as well as arthritis associated with colitis or psoriasis. It should be therefore appreciated that the compositions and methods of the present invention are also applicable for these conditions as well.

Therefore, according to another embodiment, the compositions and methods of the invention may be used for the treatment and/or amelioration of Juvenile idiopathic arthritis (JIA). JIA, is the most common form of persistent arthritis in children. (Juvenile in this context refers to an onset before age 16, idiopathic refers to a condition with no defined cause, and arthritis is the inflammation of the synovium of a joint). JIA is a subset of arthritis seen in childhood, which may be transient and self-limited or chronic. It differs significantly from arthritis commonly seen in adults (rheumatoid arthritis), and other types of arthritis that can present in childhood which are chronic conditions (e.g. psoriatic arthritis and ankylosing spondylitis).

According to another embodiment, the compositions and methods of the invention may be used for the treatment and/or amelioration of Gout. Gout (metabolic arthritis) is a disease created by a buildup of uric acid. In this condition, crystals of monosodium urate or uric acid are deposited on the articular cartilage of joints, tendons and surrounding tissues. These crystals cause inflammation and pain, both severe. If untreated, the crystals form tophi, which can cause significant tissue damage. Pseudo gout is a condition which is caused by calcium crystals. When calcium crystals cause attacks of inflammation in tendons it is called 'calcific tendinitis', The invention further provides compositions and methods for the treatment of this disorder as well.

Generally, as also disclosed above, there are many types of arthritis, it should be noted that the methods and compositions of the invention may be also applicable for treating in addition to all primary forms of arthritis indicated, also to all secondary forms of arthritis. These conditions may include Lupus erythematosus, Henoch-Schönlein purpura, Psoriatic arthritis, Reactive arthritis, Haemochromatosis, Hepatitis, Wegener's granulomatosis (and many other vasculitis syndromes), Lyme disease, Familial Mediterranean fever, Hyperimmunoglobulinemia D with recurrent fever, TNF receptor associated periodic syndrome and Inflammatory bowel disease (Including Crohn's Disease and Ulcerative Colitis).

As shown by the following Examples, the compositions of the invention significantly reduce disease severity of autoimmune and inflammatory disorders. It should be therefore noted that the composition of the invention inhibits exacerbation of inflammatory or autoimmune diseases. According to another embodiment, the composition of the invention may be used for passive immunization against an immune-related disorder.

It should be further noted that the antibodies of the invention may be provided in the form of compositions for use in passive immunization. While such compositions are generally administered by injection, it is not intended that the present invention be limited to this route alone. In general, however, the compositions of the invention are administered by intramuscular or subcutaneous injection. Occasionally, the intravenous or intraperitoneal routes may also be used to administer the compositions of the invention.

In addition to the active ingredient (i.e. the antibody), the compositions of the invention may also comprise a buffering agent, an agent which adjusts the osmolarity thereof, and optionally, one or more further additives, such as carriers, as known in the art.

As shown by the following Examples, the antibodies of the invention clearly exhibit an anti-inflammatory effect. More specifically, the invention show that exposure of macrophages to anti-peptide 6 antibodies elicits sequential events resulting eventually in the up-regulation of the IL-10 gene expression. The increase of IL-10 secretion in the inflammatory site can divert the local cytokine profile from an inflammatory to an anti-inflammatory response and thus may explain the mechanism of protection against inflammation rendered by these antibodies.

Induction of IL-10 secretion is a direct effect of the interaction of the antibodies with macrophage proteins and does not require the presence of any HSP antigen. The anti-peptide 6 monoclonal antibodies bind specifically to human macrophage membrane proteins, as illustrated in FIGS. 12A and 12B. Thus, the antibodies of the invention may be used as immunomodulators, modulating the Th1/Th2 cell balance towards an anti-inflammatory Th2 response. Therefore, the invention further provides a composition for increasing the expression and levels of IL-10 (Interleukine-10). According to this aspect, the composition of the invention comprises as an active ingredient an effective amount of at least one isolated and purified antibody directed against a peptide consisting of the amino acid sequence of SEQ ID. NO. 1 or against biologically functional homologues and derivatives thereof. The composition of the invention may optionally comprise a pharmaceutically acceptable carrier, excipient or diluent. According to one embodiment, the biologically functional homologues and derivatives of the peptide o SEQ ID NO. 1 may be selected from the group consisting of SEQ ID. NO. 2 and SEQ ID. NO. 3.

Thus, according to a specific embodiment, the IL-10 enhancing composition of the invention may comprise as an active ingredient any of the antibodies of the invention, specifically, any one of the antibodies directed against the peptides of SEQ ID NO. 1, 2 or 3, or any combinations or mixtures of said antibodies.

According to another specific embodiment, the IL-10 enhancing composition of the invention comprises at least one antibody specifically directed against peptide-6 that is also indicated herein as the peptide of SEQ ID NO. 2.

As indicated above, the enhanced expression of IL-10 may modulate the Th1/Th2 balance towards the Th2 anti-inflammatory response. Therefore, the antibodies of the invention may be useful in conditions where modulation of the Th1/Th2 balance towards an anti-inflammatory reaction is desired. Thus, according to one embodiment, the compositions of the invention may be used for increasing the expression and levels of IL-10 in a subject in need thereof, thereby modulating the Th1/Th2 cell balance towards an anti-inflammatory Th2 response in the treated subject. According to one specific embodiment, such subject is a subject suffering of an immune-related disorder. For example, an immune-related disorder such as an autoimmune disease, (for example, Arthritis, multiple sclerosis (MS), Type-1 diabetes, lupus, Graves disease and thyroiditis, IBD), graft rejection pathology and graft versus host disease, and disorders induced by supper antigens, such as toxic shock, septic shock and severe sepsis.

It should be further appreciated that in general, the composition as well as the methods of the present invention may be used in the treatment of any autoimmune disease such as for example, but not limited to, Eaton-Lambert syndrome, Goodpasture's syndrome, Greave's disease, Guillain-Barr syndrome, autoimmune hemolytic anemia (AIHA), hepatitis, insulin-dependent diabetes mellitus (IDDM), systemic lupus erythematosus (SLE), multiple sclerosis (MS), myasthenia gravis, plexus disorders e.g. acute brachial neuritis, polyglandular deficiency syndrome, primary biliary cirrhosis, rheumatoid arthritis, scderoderma, thrombocytopenia, thyroiditis e.g. Hashimoto's disease, Sjogren's syndrome, allergic purpura, psoriasis, mixed connective tissue disease, polymyositis, dermatomyositis, vasculitis, polyarteritis nodosa, polymyalgia rheumatica, Wegener's granulomatosis, Reiter's syndrome, Behget's syndrome, ankylosing spondylitis, pemphigus, bullous pemphigoid, dermatitis herpetiformis, insulin dependent diabetes, inflammatory bowel disease, ulcerative colitis and Crohn's disease.

According to another aspect, the invention relates to a method for the treatment or amelioration of an immune-related disorder. The method of the invention comprises the step of administering to a subject in need thereof a therapeutically effective amount of at least one isolated and purified antibody directed against a peptide consisting of the amino acid sequence of SEQ ID. NO. 1 or against biologically functional homologues and derivatives thereof, or of a composition comprising the same. According to one embodiment, the biologically functional homologues and derivatives of the peptide of SEQ ID NO. 1 may be selected from the group consisting of SEQ ID. NO. 2 and SEQ ID. NO. 3. Thus, it should be appreciated that the method of the invention may use any of the antibodies of the invention, specifically, antibodies directed against the peptides of SEQ ID NO. 1, 2 or 3, or any combinations or mixtures of such antibodies. According to one particular embodiment, an anti-peptide 6 antibody (the peptide of SEQ ID NO. 2) may be used for the method of the invention.

According to one embodiment, the method of the invention may be specifically applicable for treating immune-related disorder, specifically, an autoimmune or inflammatory disorder.

According to another embodiment, the method of the invention may be applied for treating an inflammatory disorder, specifically, an inflammatory arthritis.

According to one embodiment, the method of the invention leads to inhibition of exacerbation of the autoimmune and inflammatory disorders, thereby significantly reducing disease severity.

According to another embodiment, the method of the invention may be used for passive immunization against an immune-related disorder.

In another aspect, the invention provides a method for increasing the expression and levels of IL-10 in a subject in need thereof. The method of the invention comprises the step of administering to the treated subject a therapeutically effective amount of at least one isolated and purified antibody directed against a peptide consisting of the amino acid sequence of SEQ ID. NO. 1 or against biologically functional homologues and derivatives thereof, or of a composition comprising the same. According to one embodiment, the biologically functional homologues and derivatives of said peptide are selected from the group consisting of SEQ ID NO. 2 and SEQ ID. NO. 3. Thus, the method of the invention may use any of the antibodies of the invention, specifically, antibodies directed against the peptides of SEQ ID NO. 1, 2 or 3.

In one specific embodiment, an isolate and purified antibody directed specifically against peptide-6 (also denoted by SEQ ID NO. 2), may be used by the method of the invention for increasing the expression and levels of IL-10 in a subject in need thereof. This may be useful in conditions where modulation of the Th1/Th2 balance towards an anti-inflammatory reaction is desired. Many inflammatory autoimmune diseases other than RA are induced by similar pathogenic immune and inflammatory processes. Those diseases include inflammatory joint diseases such as Juvenile Idiopathic Rheumatoid Arthritis, psoriatic arthritis, and spondyloarthritis and other organ specific autoimmune diseases such as inflammatory bowel disease (IBD) and psoriasis. Indeed all of them respond to similar anti-inflammatory drugs including the anti-TNF biological agents that suppress the TNF inflammatory cytokine and change the equilibrium between inflammatory and anti-inflammatory cytokines. Moreover IL-10 deficient mice develop spontaneous colitis. Therefore the therapeutic approach presented by the invention is based on upregulation of the anti-inflammatory IL-10 cytokine, is expected to be effective in these diseases as well.

It should be further appreciated that the invention further provides a method for increasing either in vivo, in vitro or ex-vivo, the levels and the expression of IL-10 by immune cells, specifically macrophages. Such macrophages may be obtained from a subject suffering from an immune-related disorder. According to one embodiment, the method of the invention comprises the step of contacting these cells under suitable conditions with at least one of the antibodies of the invention, specifically, antibodies directed against the peptide of SEQ ID NO. 1, 2 or 3, or any combination of these antibodies.

According to a specifically preferred embodiment, the compositions and methods of the invention is specifically applicable in enhancing and increasing the expression of the anti-inflammatory cytokine, IL-10.

According to one embodiment, wherein indicate "increasing" or "enhancing" the expression or the levels of an anti-inflammatory cytokine, specifically of IL-10, it is meant that such increase or enhancement may be an increase or elevation of between about 10% to 100% of the expression of such cytokines. Particularly, an increase of 10%, 15%, 20%, 25%, 30%, 35%, 40%, 45%, 50%, 55%, 60%, 65%, 70%, 75%, 80%, 85%, 90%, 95% or 100% of the expression as compared to a suitable control. It should be further noted that increase or elevation may be also an increase of about 2 to 100 folds. Still further, it should be appreciated that the increase of the levels or expression of said IL-10 cytokine may be either in the transcription, translation or the stability of said cytokine.

According to another embodiment, the composition of the invention may be used for modulating the balance between Th1/Th2 towards the Th2 anti-inflammatory reaction in a subject in need thereof.

Therefore, the use of the composition of the invention for the treatment of an immune-related disorder in a subject in need thereof is further provided.

More specifically, the invention provides a composition for the treatment of immune disorders related to an imbalance in the Th1-Th2 response. An immune-related disorder may be for example, an autoimmune disease, (for example, Arthritis, multiple sclerosis (MS), Type-1 diabetes, lupus, Graves disease and thyroiditis, IBD), graft rejection pathology and graft versus host disease, inflammatory disorders and disorders induced by supper antigens, such as toxic shock, septic shock and severe sepsis.

The following Examples show the anti-MT HSP antibody response of various rats and its correlation with susceptibility to induction of arthritis. Only a limited number of epitopes in the bacterial HSP molecule is recognized by rat antibodies. Resistant strains were found to respond to peptides that are found on the outer surface of the molecule, as well as to the whole molecule. On the other hand, antibodies from naive Lewis rats reacted with a smaller number of peptides, which are less exposed on the outer surface of the molecule and did not react with the intact HSP. The presence of antibodies against some of the epitopes, as well as the whole MT-HSP, may be associated with resistance to the induction of arthritis and they were therefore named "protective" epitopes.

It has been previously reported that the T cell response to bacterial HSP shows determinant spreading. The present data, given in the following Examples, show that there is a clear B cell determinant spreading as well, and this spreading can occur also spontaneously, namely without intentional vaccination. The B cell epitopes, as will be shown, are different from the T cell epitopes. This observation is of particular significance to the present invention.

Young naive Lewis rats recognized only two bacterial epitopes; peptides 40 and 63. Four months Lewis rats recognized, in addition, peptides 36 and 45 and nine months Lewis rats recognized peptides 6, 7 and 31, in addition to all the other mentioned peptides. Recognition of these peptides by the nine months Lewis rats is also associated with recognition of the whole bacterial HSP molecule.

The B cell epitope repertoire of the young BN rats is similar to that of the old Lewis rats including only one additional peptide, peptide 59. Lewis rats that were immunized with the CFA responded to all the aforementioned peptides, as well as to two additional peptides, namely 21 and 84.

Although all the anti HSP peptide antibodies found in naive old Lewis rats and in naive young BN rats are referred to as natural antibodies, it is possible that they are elicited as a response to the exposure of these rats to environmental pathogens (as "natural" antibodies may indeed always be) and that the epitope spreading in response to these pathogens occurs in the BN rat more rapidly, earlier and in more strongly than in the Lewis rat. Lewis rats have to be immunized with CFA in order to mimic the natural response of the BN rats. The similarity of the antibody repertoire of the naive BN rats to that of the immunized Lewis rat supports this possibility.

The nature of the B cell epitopes and the correlation between recognition of certain epitopes and the whole molecule can be better understood from primary and tertiary structure analysis of the molecule, shown hereafter.

To see whether the anti-HSP protective antibodies can be induced by immunization with the "protective" peptides, Lewis rats were immunized with the various peptides, without Freund's adjuvant, Immunization with three peptides, the bacterial peptides 6 and 7, and the mammalian peptide 5 (also denoted by SEQ ID NO. 2, 3 and 4, respectively), led to production of antibodies against bacterial peptide 6, as well as to an anti-HSP response, showing that antibodies against an "external" peptide will lead to recognition of the whole molecule. Induction of these antibodies also led to disease resistance.

Although the mechanism of disease resistance induced by the natural as well as the induced anti-HSP antibodies has not been yet clarified, it is possible that the antibodies against the MT HSP inhibit the early steps of induction of pathogenic T cells to the peptide by intervening in the antigen processing or the T cell recognition of the pathogenic epitopes. Alternatively, they may prevent the effector steps of the pathogenic response by binding to the self HSP-cross reacting target antigen.

The T cell response of AA susceptible Lewis and AA resistant WKA Wistar rats to the bacterial HSP 65KD has been thoroughly studied. It has been shown that in the early post immunization stages the Lewis T cells respond to several determinants found in the N terminal, as well as in the carboxy terminal of the molecule, whereas later a shift to carboxy terminal epitopes has developed. The early T cell response of Wistar rats was similar to that of the late response of the Lewis rats. As the 3D structure of the molecule does not show the carboxy and the N terminal sites to be in different locations of the molecule, it is not surprising that the B-cell epitopes were found all along the molecule without any selection of either the carboxy or the N terminal of the molecule.

A comparison between the published dominant T cell epitopes and the present B cell epitopes did not reveal common epitopes. To the contrary, the lack of natural antibodies to certain epitopes like 6, 7 or 31 in the naive Lewis rat is associated with an early T cell response to these epitopes, whereas the presence of antibodies to epitopes like 40 and 63 is associated with lack of an early T cell response. Based on these correlations, it may be suggested that the presence of natural antibodies to certain epitopes may actually inhibit T cell response to them, whereas the lack of antibodies enables the T cells to respond to these epitopes. For example, AA susceptible Lewis rats that do not have natural antibodies to the bacterial peptide 31 can develop a T cell response to this peptide, and these pathogenic T cells can induce arthritis.

As previously mentioned, there was a clear correlation between disease resistance and the presence of anti-HSP antibodies. Young naive Lewis rats did not have detectable antibodies against the HSP molecule whereas nine months old Lewis rats developed these antibodies in a significant titer. Parallel to the development of the anti-HSP response, the old rats also became resistant to induction of arthritis. Young Lewis rats acquired both the antibodies and disease resistance after immunization with CFA and the naturally resistant BN rats had anti HSP antibodies spontaneously, without the need for immunization. It is possible therefore that these antibodies bind the bacterial HSP immediately after immunization and prevent it from becoming accessible to the cellular arm of the immune system.

As noted previously, the epitopes "chosen" by the B cells from the bacterial HSP are epitopes that have relatively little homology with the self HSP, most probably as a result of tolerance to self antigens.

Analysis of the anti self (rat) HSP antibody repertoire indeed showed that there is a limited number of epitopes recognized by the rat immunoglobulins in the self HSP molecule. Naive young Lewis rats did not respond to any self peptide neither did they respond to the whole self HSP 60 molecule. BN and post-AA Lewis rats that reacted with 8-10 bacterial HSP epitopes responded to only two epitopes in the self HSP, peptides M5 and M30, as well as to the whole self HSP molecule.

Expression of the mammalian (or self) HSP is upregulated in inflamed synovia of rats with AA [Kleinau, S.K., et al., Scand. J. Immunol. 33:195-202 (1991)] and cross-reactive immune recognition has been found between the Mycobacterial HSP 65KD and endogenous self HSP 60KD at the T-cell level [Munk, M.E., et al., J. Immunol. 143:2844 (1989); Anderston, S.M., et al., Eur. J. Immunol. 23:33 (1993); Quayle, A.J., et al., Eur. J. Immunol. 22:1315-1322 (1992)].

As the anti self antibodies were found only in the resistant rats, it is possible that antibodies that cross react with the self HSP may conceal it from the pathogenic T cells and thus act as protective antibodies.

It is interesting to note that one of the two self protective epitopes is the self peptide 5, which is the homologous rat epitope to the bacterial protective peptide 6. Moreover, immunization with the bacterial peptides 6 and 7 and with the mammalian peptide 5 led to the production of anti bacterial HSP 6 and anti bacterial HSP antibodies, as well as protection against disease induction. Observing the primary structure of these three peptides leads to the conclusion that they express a common motif (V-E-W G-P) which might be the protective motif of these peptides (FIG. 5).

Therefore, the humoral immune response to the bacterial HSP may be aimed at a limited number of potential B-cell epitopes. These epitopes are peptide stretches located between amino acids that serve as bends and spacers, and are found in non-conserved parts of the molecule. Recognition of B-cell epitopes that are exposed on the surface of the molecule leads to binding to the whole molecule and is associated with resistance to induction of arthritis.

This resistance occurs naturally in some strains of rats whereas in others it can be acquired with age or upon immunization with HSP. Immunization with some of the "protecting" epitopes can lead both to disease resistance as well as to the serological profile that is present in the resistant strains.

Thus, according to a further aspect, the invention relates to a purified B cell epitope peptide consisting of the amino acid sequence of SEQ ID. NO. 1 or biologically functional homologues and derivatives thereof selected from the group consisting of SEQ ID. NO. 2 and SEQ ID. NO. 3. According to this aspect, the peptides of the invention are specifically suitable for the treatment and amelioration of an immune-related disorder.

The amino acid and nucleic acid sequences of the invention are presented in Table 1.

TABLE 1

| SEQ ID NO | Peptide NO. | Amino Acid or Nucleic Acid Sequence |
|---|---|---|
| 1 |  | GPKGRNVVLEKKWGAPTITNDG |
| 2 | 6 | GPKGRNVVLEKKWGAP |
| 3 | 7 | VVLEKKWGAPTITNDG |
| 4 | R5 | TVIIEQSWGSPKVTKDGVTV |
| 5 |  | GCCGCCATGGGACCAAAGGGACGCAAGGTGG TACTAGAGAAGAAATGGGGCGCGCCGTAGCT CGAGA |

By the term "biologically functional homologues and derivatives" is meant any variations, including deletion, substitution and/or insertion of an amino acid residue in the amino acid sequences or a nucleic acid in the nucleic acid sequences of the invention which would not alter the biological activity of the peptides, or peptides encoded by the nucleic acid sequences, against autoimmune diseases. Thus, this term is to be taken to mean peptides with similar structure, peptides or their derivatives that are recognized by the protective antibodies and/or peptides or their derivatives that can induce protective antibodies upon immunization.

Thus, the invention further provides a pharmaceutical composition for the treatment or amelioration of an immune-related disorder. According to one embodiment, the composition of the invention comprises as an active ingredient a therapeutically effective amount of at least one isolated and purified peptide consisting of the amino acid sequence of SEQ ID. NO. 1 or against biologically functional homologues and derivatives thereof, wherein the biologically functional homologues and derivatives thereof may selected from the group consisting of SEQ ID. NO. 2 and SEQ ID. NO. 3. Thus, the therapeutic composition of the invention may comprise as an active ingredient any of the peptides of SEQ ID NO. 1, 2, 3 or any combinations and mixtures thereof. It should be appreciated that the composition of the invention may optionally further comprises a pharmaceutically acceptable carrier, excipient or diluent.

According to one embodiment, the composition of the invention may be used for treating an immune-related disorder, for example, an autoimmune or inflammatory disorder.

According to one embodiment, the composition of the invention may be used for the treatment and/or amelioration of an inflammatory disorder, specifically, an inflammatory arthritis.

It has been shown that the development of autoimmune diabetes in the NOD mouse is marked by the presence of T-cells reactive to the p277 peptide of the HSP 60. It has further been shown that the p277 peptide can be used as a therapeutic vaccine to arrest NOD diabetes [Elias, D., et al., Lancet 343:704-706 (1994)]. The p277 peptide has been shown to arrest also autoimmune diabetes induced by the Streptozotocin toxin [Elias, D., et al., Diabetes 45:1168-1172 (1996)]. Likewise, the vaccines according to the invention may also be used to suppress an autoimmune disease.

Furthermore, the compositions of the invention (that may be also referred to as vaccines or vaccinating compositions) may also be used to prevent relapses of autoimmune diseases, which characterize many autoimmune diseases. Prevention of a relapse is therefore part of the therapeutic approach to these disorders. The above peptide p277 has been shown to prevent NOD mice diabetes by turning off the anti-p277 immunity early in life. It was later shown to arrest autoimmune process even after it is far advanced [Elias (1994) ibid.].

As shown by Example 5, active immunization with the bacterial HSP peptide 6 (SEQ ID. NO 2) is also beneficial in autoimmune disorders, for instance autoimmune diabetes. NOD mice immunized with the mycobacterial peptide 6 produced antibodies against the peptide 6 and the whole HSP 65. The protective effect of these immunoglobulins is reflected by the delayed appearance of the diabetic symptoms and the significantly lower number of sick mice in the vaccinated group.

According to another specific embodiment, the composition of the invention may be used for the treatment and/or amelioration of an autoimmune disorder, such as diabetes.

Diabetes mellitus, is a syndrome characterized by disordered metabolism and inappropriately high blood sugar (hyperglycaemia) resulting from either low levels of the hormone insulin or from abnormal resistance to insulin's effects coupled with inadequate levels of insulin secretion to compensate. The characteristic symptoms are excessive urine production (polyuria), excessive thirst and increased fluid intake (polydipsia), and blurred vision; these symptoms are likely absent if the blood sugar is only mildly elevated.

There are three main forms of diabetes: type 1, type 2 and gestational diabetes (occurs during pregnancy). Type 1 diabetes mellitus is characterized by loss of the insulin-producing beta cells of the islets of Langerhans in the pancreas, leading to a deficiency of insulin. The main cause of this beta cell loss is a T-cell mediated autoimmune attack. There is no known preventative measure that can be taken against type 1 diabetes. Most affected people are otherwise healthy and of a healthy weight when onset occurs. Sensitivity and responsiveness to insulin are usually normal, especially in the early stages. Type 1 diabetes can affect children or adults and was traditionally termed "juvenile diabetes" as it represents a majority of cases of diabetes affecting children.

The principal treatment of type 1 diabetes, even from the earliest stages, is replacement of insulin combined with careful monitoring of blood glucose levels using blood testing monitors. Without insulin, diabetic ketoacidosis can develop and may result in coma or death. Emphasis is also placed on lifestyle adjustments (diet and exercise) though these cannot reverse the loss. Apart from the common subcutaneous injections, it is also possible to deliver insulin by a pump, which allows continuous infusion of insulin 24 hours a day at preset levels, and the ability to program doses (a bolus) of insulin as needed at meal times.

Type 1 treatment must be continued indefinitely. Treatment does not impair normal activities, if sufficient awareness, appropriate care, and discipline in testing and medication are taken.

The prevalence rate in the USA is 0.12% of the population or nearly 340,000 people. The incidence rate is about 30,000 annual cases, 0.01% of the population.

The invention also relates to a vaccine comprising as active ingredient an effective vaccinating amount of at least one peptide of the invention. The vaccines of the invention are particularly intended to confer immunity against inflammatory and autoimmune diseases, for example, inflammatory arthritis or diabetes.

By the term "effective vaccinating amount" is meant an amount sufficient to stimulate the immune system, directly or indirectly, and confer immunity against inflammatory and autoimmune diseases. Such effective amount is determined the severity of the disease, age, sex and weight of the patient, as well as the patient's general condition, and by other considerations known to the attending physician. Preferred doses, per injection, may be about 0.001 to 100 mg/Kg body weight, specifically, 0.02-2 mg/Kg body weight.

The vaccines according to the invention may optionally further comprise pharmaceutically acceptable carriers, diluents additives, excipients and adjuvants. By the terms "pharmaceutically acceptable carriers, diluents additives, excipients and adjuvants" is meant any inert, non-toxic material that may assist in the efficient delivery of the active ingredient.

It should be further noted that the invention further relates to DNA constructs comprising the nucleic acid sequence of the invention or functional homologues and derivatives thereof. The constructs of the invention may further comprise additional elements such as promoters, regulatory and control elements, translation, expression and other signals, operably linked to the nucleic acid sequence of the invention.

In yet another aspect, the invention provides a method for the treatment or amelioration of an immune-related disorder comprising the step of administering to a subject in need thereof a therapeutically effective amount of at least one isolated and purified peptide of any one of SEQ ID NO. 1, 2, 3, or any combinations and mixtures thereof, or of a composition comprising the same.

According to one embodiment, the method of the invention may be particularly intended for the treatment of an immune-related disorder, for example, an autoimmune or inflammatory disorder.

According to one specific embodiment, the method of the invention may be particularly applicable for treating an inflammatory disorder, specifically, an inflammatory arthritis.

In yet another embodiment, the method of the invention may be particularly applicable for treating an autoimmune disorder. According to one specific embodiment, such disorder may be diabetes.

According to one embodiment, the peptides of the invention and particularly the peptide of SEQ ID NO. 2 are capable of significantly suppressing disease severity of an immune-related disorder. In yet another embodiment, the peptides of the invention and any compositions thereof are used in methods and compositions for the active immunization of a subject in need thereof, against an immune-related disorder.

The invention thus further relates to vaccines or vaccinating compositions comprising as active ingredient an effective vaccinating amount of at least one peptide of the invention.

The vaccines of the invention are particularly useful for conferring immunity against autoimmune or inflammatory disorders.

By "patient" or "subject in need" used by the invention to describe any of the compositions and methods of the invention, it is meant any mammal who may be affected by the above-mentioned conditions, and to whom the treatment methods and compositions herein described is desired, including human, bovine, equine, canine, murine and feline subjects. Preferably said patient is a human. Administering of the compositions of the invention to the patient includes both self-administration and administration to the patient by another person.

According to another specific embodiment, the active ingredients, either the antibodies or the peptides used by the invention, or any compositions thereof, may be administered via any mode of administration. For example, oral, intravenous, intramuscular, subcutaneous, intraperitoneal, parenteral, transdermal, intravaginal, intranasal, mucosal, sublingual, topical, rectal or subcutaneous administration, or any combination thereof.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician.

It should be noted that any of the pharmaceutical compositions of the invention, may comprise the active compound (either the antibodies or the peptides of the invention), in free form and be administered directly to the subject to be treated. Alternatively, depending on the size of the active molecule, it may be desirable to conjugate it to a carrier prior to administration. Therapeutic formulations may be administered in any conventional dosage formulation. Formulations typically comprise at least one active ingredient, as defined above, together with one or more acceptable carriers thereof.

Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intraperitoneal (IP), intravenous (IV) and intradermal) administration.

The pharmaceutical forms suitable for injection use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

In the case of sterile powders for the preparation of the sterile injectable solutions, the preferred method of preparation are vacuum-drying and freeze drying techniques which yield a powder of the active ingredient plus any additional desired ingredient from a previously sterile-filtered solution thereof.

The pharmaceutical compositions of the invention generally comprise a buffering agent, an agent who adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

The pharmaceutical compositions of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers. The pharmaceutical compositions of the present invention also include, but are not limited to, emulsions and liposome-containing formulations.

The nature, availability and sources, and the administration of all such compounds including the effective amounts necessary to produce desirable effects in a subject are well known in the art and need not be further described herein. The preparation of pharmaceutical compositions is well known to the skilled man of the art and has been described in many articles and textbooks, see e.g., Remington's Pharmaceutical Sciences, Gennaro A. R. ed., Mack Publishing Co., Easton, Pa., 1990, and especially pp. 1521-1712 therein.

According to one embodiment, a buffering agent may be phosphate-buffered saline solution (PBS), which solution is also adjusted for osmolarity.

In another embodiment, the composition is one lacking a carrier. Such formulations are preferably used for administration by injection, including intramuscular and intravenous injection.

It should be noted that the amount of the therapeutic or pharmaceutical composition of the invention which is effective in the treatment of a particular disease, condition or disorder will depend on the nature of the disease, condition or disorder and can be determined by standard clinical techniques. In addition, in vitro assays as well as in vivo experiments may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems.

For administration by injection, the formulations may be presented in unit dosage form, e.g. in ampoules or in multi-dose containers with an added preservative.

The compositions of the invention can also be delivered in a vesicle, for example, in liposomes. In another embodiment, the compositions can be delivered in a controlled release system.

As used herein, in the specification and in the claims section below, the term "treat" or treating and their derivatives includes substantially inhibiting, slowing or reversing the progression of a condition, substantially ameliorating clinical symptoms of a condition or substantially preventing the appearance of clinical symptoms of a condition.

Therefore, in a further embodiment, the compositions and methods of the invention may be useful for treatment of or amelioration of inflammatory symptoms in any disease, condition or disorder where immune and/or inflammation suppression is beneficial such as, but not limited to, inflammatory arthritis, specifically, Rheumatoid arthritis and autoimmune conditions, such as diabetes.

As shown by Examples 6 and 12, serum samples obtained from diabetic and RA patients, respectively, exhibited significantly lower amounts of ant-peptide 6 antibodies, as compared to healthy control subjects. It should be therefore appreciated that the invention may also provide a diagnostic method for monitoring and diagnosing these conditions.

The present invention can also provide a method for the prediction of susceptibility/predisposition to develop inflammatory or autoimmune conditions. In the rat system, it has been shown that naive young Lewis rats do not have antibodies against peptide 6 of the HSP and that they are susceptible to the development of arthritis after exposure to or immunization by HSP. In a similar manner, healthy individuals that lack sub-groups of antibodies against HSP specific peptides may be susceptible to onset of arthritis.

"Naturally" occurring anti-peptide 6 and anti-HSP antibodies are found in serum samples of normal controls and RA patient Although total immunoglobulin G amounts as well as anti-HSP antibody level are similar in both groups, anti-peptide 6 antibodies were found to be significantly lower (by 3 fold) in RA patients.

The present invention also provides an assay for the assessment and determination of susceptibility/predisposition to arthritis. The assay can be performed by ELISA, in which the peptides are bound to the solid phase and serum samples added, followed by adding anti human immunoglobulins. Other known immunological analysis techniques can also be used.

Still further, this invention provides a method for monitoring the patient's disease development and the possibility to evaluate the prognosis. This information can be of major importance in the decision of patient treatment course and the doses of the medication to be used. Assessment of anti-peptide 6 in patient's serum can be performed by ELISA or any other sensitive immune assay capable to detect antibodies.

The term "monitoring" used in connection with the present invention relates to a close ongoing medical surveillance complemented with periodical medical tests, to assess the disease course and severity.

The term "diagnosis" refers to the act of recognizing the presence of a disease from its signs or symptoms. In the present invention, diagnosis for Rheumatoid arthritis or diabetes can be performed based on the results obtained using any immunological assays (colorimetric, fluorescent, magnetic, chemoluminescent or radioactive) capable of measuring antibodies amount, such as ELISA.

By the term "prognosis" used in the present application is meant predicting the course and termination of a disease.

As described above, the present invention provides methods and compositions for the treatment of inflammatory and autoimmune disease. Active and passive vaccination using the peptides of the invention, specifically, peptide 6 (SEQ ID. NO. 2), or the antibodies of the invention, specifically, the anti-peptide 6 antibodies induce a specific immune response that upon restriction to the inflammatory sites, may provide a specific localized treatment for inflammatory and autoimmune diseases. This specific treatment, in contrast to commonly used generalized anti-inflammatory drugs, may allow the use of small therapeutic doses and to avoid the drugs' secondary effects.

The invention will be described in more detail on basis of the following Examples, which are illustrative only and do not in any way limit the invention. Many modifications and variations of the present invention are possible in light of the present teachings. It is therefore understood, that within the scope of the appended claims, the invention may be practiced otherwise than specifically described.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Animals:

Female inbred Lewis rats, 6 weeks or 9 months old, were obtained from Harlan Lab. Israel. Female Brown-Norway (BN) rats, 6 weeks old, were obtained from Harlan Sprague-Dawley, USA.

Antigens and Antibodies:

Recombinant HS P65 of *Mycobacterium Tuberculosis* was a gift from Dr. M. Singh (The WHO Recombinant Protein Bank, Germany). Recombinant mammalian HSP 60 was purchased from StressGen Biothec. Corp. (Victoria, BC, Canada). Synthetic peptides of MT HSP 65 were a gift from Dr. L. Adorini (The Roche Milano Ricerche, Milano, Italy). Synthetic peptides 6 and 7 of MT HSP 65 and R5 of mammalian HSP 60, (SEQ ID: NOs. 2, 3 and 4 respectively) were synthesized by standard solid phase 9-FMOC technology. The peptides were purified by reverse phase HPLC and analyzed by Fast Atom Bombardment Mass spectrometry at the Weizmann Institute, Rehovot, Israel.

Synthetic peptides of the mammalian HSP 60 were a gift from Dr. I. Cohen (The Weizmann Institute, Rehovot, Israel).

Goat anti Rat IgG conjugated to alkaline-phosphatase was purchased from Jackson ImmunoResearch Lab. Inc. (Avonsdale, Pa.).

Induction and Clinical Assessment of Adjuvant Arthritis:

Lewis rats were injected with 1 mg of *Mycobacterium Tuberculosis* H37Ra (Difco, Detroit, Mich.) in Complete Freund's Adjuvant (Difco) subcutaneously at the base of the tail. Severity of Arthritis (arthritis index) was assessed blindly as follows: 0—no arthritis; 1—redness of the joint; 2—redness and swelling of the joint. The ankle and tarsal-metatarsal joints of each paw were scored. A maximum score of 16 can be obtained, but a score above 8 indicates a severe disease.

Dot Blots Assay:

Antigens were dissolved in PBS and samples of 1 μg were adsorbed on Nitrocellulose paper. The paper was air-dried and incubated with BSA 1% in PBS for 20 min. to block non-specific binding. The samples were then washed in PBS-Tween 0.05% and incubated with rat sera diluted 1:100 in BSA-PBS, for 90 min. at room temp. Samples were washed and incubated with goat anti rat antibody conjugated to alkaline phosphatase diluted 1:1000 in BSA-PBS for 90 min. at RT. After re-washing the color reaction was developed by adding a mixture of BCIP-NBT (Sigma-Fast, Sigma) to the cells for 15 min. The reaction was stopped by the addition of tap water.

ELISA:

Flat-bottomed 96 well plates (Corning) were coated with mammalian HSP 60 or Mycobacterial HSP 65 (10 μg/ml) in carbonate buffer pH 9.6 overnight at 4° C.

After extensive washing with PBS-Tween 0.05% plates were incubated with blocking buffer containing 1% BSA (Sigma) for 60 min. at RT.

HSP peptides were attached to plates pre-treated with glutaraldehyde according to Kasprzyk et al. [Kasprzyk, P. G., et al., Anal. Biochem. 174:224 (1988)]. Shortly, plates were coated with 100 μl well of 5% w/v of glutaraldehyde in PBS for 1 hour at room temp. Plates were washed thoroughly with PBS and peptides (1 μg/100 μl) were added to each well, incubated overnight at 4° C. Plates were shaken dry and blocked with BSA 1% in PBS.

Plates coated with either HSP or peptides were washed again and incubated with rat sera diluted 1:100 with PBS-Tween 0.01% for 90 min. at room temp. After re-washing the plates were incubated with Goat anti rat IgG or IgM conjugated to alkaline-phosphatase for 60 min. at room temp. The presence of antibodies was revealed by addition of the substrate PNP (NP 100, Chemicon, Temecula, Calif.) to the plates. Optical density was measured photometrically at 405 nm.

Preparation of Human Monoclonal Anti-Peptide 6 Antibodies:

Human monoclonal anti-peptide 6 antibodies are prepared by the following technique: blood samples are collected from healthy volunteers and they are tested for the presence of anti-peptide 6 antibodies (by a specific ELISA for peptide 6). B cells from positive individuals are transformed by EBV according to the method of Steinitz et al. [Steinitz, M. In: Immunoassay technology. R. S. Pal (ed.) Macmillan Press U.K. pp-1-17 (1988)]. Anti-peptide 6 positive clones are re-cloned and expanded.

Western Blot Analysis of Human Macrophages Proteins Fractions Using Anti-Peptide 6 Monoclonal Antibodies Human macrophages are purified from human peripheral blood. The WBC are separated from RBC by Ficoll and incubated in RPMI medium containing 2% human serum at 37° C. for 9 minutes. After the incubation, non-adherent lymphocytes cells are washed away with PBS, leaving only adherent macrophages cells in the tissue culture plate.

Hydrophilic Membrane, Hydrophobic Membrane and Cytoplasmic proteins, are purified from the human macrophages cell using ReadyPrep™ Protein Extraction kit (Membrane I) and ReadyPrep™ Protein Extraction kit (Cytoplasmic) (Bio-Rad Laboratories, Inc., Hercules, Calif. 94547, USA).

Ten micrograms (10 μg) of each macrophage protein fractions are boiled in sample buffer containing SDS and β-mercaptoethanol and resolved at 9% SDS-PAGE The separated proteins are transferred to nitrocellulose by the Western blot technique and incubated with supernatant from a rat anti-peptide 6 antibody secreting hybridoma (clone B-24). Total rat IgG (10 μg/ml) are used as negative control. The binding intensity was detected by Goat anti-rat IgG and IgM Fc Peroxidase conjugated (HRP) (Jackson Immunoresearch Laboratories, Inc., West Grove, Pa. 19390, USA) were used as secondary antibodies and the signal was developed using a chemiluminescence detection system.

Amino Acid Comparison:

"Pileup" and "pretty" programs (GCG—Wisconsin package, v.9.0) were used to compare amino acid sequences of three HSP 60 (*Mycobacterium Tuberculosis*, rat and human).

Structure Analysis:

RasMol. v. 2.6 program and the 3D structure of the *E. coli* complex GroEL-GroES (pdb ID: 1AON reference) were used to analyze the position of epitopes.

Since the crystal structure of MT HSP 65KD is not yet completely known, a three-dimensional model for the tertiary structure of MT HSP 65KD based on the solved crystal structure of GroEL from *E. coli* (pdb ID: 1GRL) was used as template. This model was built by programs for comparative protein modeling.

Modulation of AA by Mycobacterial and Mammalian HSP Peptides:

HSP 65 derived peptides were tested for their ability to modulate the appearance or severity of AA in Lewis rats. Rats were immunized with 100 μg of each peptide in PBS, three weeks (3W), 2W and 1W before induction of AA by MT. Control rats received PBS. Rats were bled for testing antibody presence before injection of MT and 30 days post MT injection.

DNA Vaccine Preparation:

A synthetic oligoDNA, having the SEQ ID: NO. 5, encoding the oligopeptide *Mycobacterium Tuberculosis* HSP 65KD NO. 6, presented in Table 1, was cloned into the commercially available mammalian expression vector, pTARGET (Promega, Madison, Wis., USA), having the restriction map depicted in FIG. 6. The cloning was carried out according to the manufacturer's instructions.

The plasmid construct was then transferred into *E. coli* JM109 strain and expanded to large scale for further plasmid purification, using the DNA purification system Wizard Plus Maxipreps kit (Programa, Madison, Wis., USA).

Animal Vaccination:

Lewis rats were pre-treated with Bupivaccine (Astra) two days prior to vaccination and later disease induction. The rats were then twice injected with 100 μg of the DNA construct, into the tibialis anterior muscle, with a week interval between the injections.

Example 1

The Interaction of Rat Immunoglobulins with Whole Mycobacterial HSP 65 and Its Peptides Previous experiments conducted by the inventors showed that immunoglobulins from AA resistant naive rats (i.e. BN or Fisher) as well as Lewis rats that recovered from AA (post AA Lewis rats), were able to suppress the induction of AA in naive Lewis rats and bound to the bacterial HSP 65 in a dot blot assay. To obtain a more quantitative evaluation of this binding, the interaction of immunoglobulins from these rats with the whole molecule of the Mycobacterial HSP 65, known to be associated with AA in Lewis rats, was tested by Dot-Blot and ELISA.

It was found that immunoglobulins from 6-8 week old BN rats, and post AA Lewis rats, reacted strongly with the HSP while no reaction was found when immunoglobulins from naive Lewis rats were tested. Interestingly, it was found that immunoglobulins from nine months old naive Lewis rat also reacted with the HSP.

To define the epitopes recognized by the anti bacterial HSP antibodies, the inventors tested by Dot-Blot the interaction of immunoglobulins from naive young BN rats and post AA Lewis rats with 90 16-mer synthetic peptides of the Mycobacterial 65KD HSP. Immunoglobulins from naive young Lewis rats served as control.

Only 10 peptides out of the 90 peptides tested (Table 2) reacted with the immunoglobulins tested. All of the rats immunoglobulins reacted with two peptides: 40 (residues 235-250) and 63 (residues 373-388). When these rats age, they acquire antibodies against additional peptides, and a similar profile to that of old Lewis rats is found in young naive BN rats, and Lewis rats that were immunized with CFA reacted also with peptides 21 (residues 121-136) and 84 (residues 499-514). It is noted that although naive Lewis rats do not recognize the whole molecule of HSP 65KD, its immunoglobulins can interact with certain peptides of this molecule, without any effect on susceptibility to AA.

TABLE 2

Antibodies to Mycobacterial HSP 65 Peptides

| Strain | 21 121-136 SEQ ID #10 | 84 499-514 SEQ ID #17 | 59 349-364 SEQ ID #15 | 7 37-52 SEQ ID #3 | 31 181-196 SEQ ID #11 | 6 31-46 SEQ ID #2 | 36 211-226 SEQ ID #12 | 45 265-280 SEQ ID #14 | 40 236-251 SEQ ID #13 | 63 373-388 SEQ ID #16 | HSP 65 | Disease Susceptibility |
|---|---|---|---|---|---|---|---|---|---|---|---|---|
| Lew-6w | − | − | − | − | − | − | − | − | + | + | − | 8/10 |
| Lew-4m | − | − | − | − | − | + | + | + | + | + | − | 3/5 |
| Lew-9m | − | − | − | + | ++ | + | + | + | ++ | +++ | + | 0/7 |
| BN-6w | − | − | + | + | + | + | ++ | + | ++ | + | +++ | 0/10 |
| Lew-Post AA | + | + | +++ | + | ++ | +++ | +++ | ++ | ++ | ++ | ++ | 0/10 |

O.D: <0.15 = −; 0.16-0.45 = +; 0.46-0.75 = ++; >0.75 = +++

Example 2

Binding of Rat Immunoglobulins with the Mammalian HSP 60 and Its Peptides

Previous studies have shown that certain bacterial HSP peptides may trigger self HSP reactive T-cells with disease suppressive regulatory potential. To analyze the anti self-HSP antibody repertoire of these rats, the reactivity of Ig's from naive and post AA Lewis rats as well as from naive BN rats to whole mammalian HSP 60 was tested by ELISA.

The results presented in Table 3 indicate that that naive and four months old Lewis rats do not possess anti self-HSP 60 antibodies, whereas nine months old Lewis rats, young BN rats and post-AA Lewis rats had significant binding to the self-HSP (Table 3). Some naive Lewis rats had very low concentrations of the antibodies.

TABLE 3

Antibodies to Mammalian HSP 60 Peptides

| Strain | Peptide Sequence | | | Disease |
| | M 5 61-80 | M 30 436-455 | M-HSP 60 | Susceptibility |
|---|---|---|---|---|
| Lew-6w | − | − | − | 8/10 |
| Lew-4m | − | − | − | 3/3 |
| Lew-9m | ++ | ++ | + | 0/7 |
| BN-6w | + | + | + | 0/10 |
| Lew-Post AA | +++ | ++ | + | 0/10 |

O.D.: <0.15 = −; 0.16-0.45 = +; 0.46-0.75 = ++; >0.75 = +++

Immunoglobulins from naive Lewis and BN rats and post-AA Lewis rats were tested for binding to 38 synthetic 20-mer peptides of the mammalian HSP 60 by Dot-Blot. It was found that immunoglobulins derived from BN and post-AA Lewis rats, but not from naive Lewis rats, reacted with 2 peptides only: peptide 5 (residues 61-80) and peptide 30 (residues 436-455). Quantitative analysis of this binding as well as the binding of immunoglobulins from four and nine month old Lewis rats confirmed the dot blot findings (Table 3).

Example 3

Amino Acid Comparison

The HSP 60 family is highly conserved: MT-HSP 65 and its mammalian homologues (rat or human) show 48% identity. In FIG. 1, the three amino acid sequences of the MT-HSP 65, HSP 60 from rat and human are compared. The consensus sequence of these three proteins is shown too. The epitopes that were found to be relevant in this study are shown in Bold and Underlined.
3D Structure Analysis
Tertiary structure plays an important role for B-cell epitope recognition. In a first approach, a simple computer program was provided, that could predict where to find potential B-cell epitopes by screening the primary structure of the peptide. The algorithm is based on a previous analysis by Warren et al. [Warren, K. G., et al., Proc. Natl. Acad. Sci. USA 92:11061 (1995)] of the Myelin Basic Protein to locate potential epitopes for B-cell. According to their analysis, two sorts of amino acids can be defined:

"Molecular spacers": These are short-chain residues (side chains of one carbon or less) that could provide a molecular gap for adjacent long-chain amino acids. Three amino acids that fit this definition are: Glycine (G), Alanine (A) and Serine (S).

"Molecular bends": Proline (P) residues that can cause disruptions in secondary structure.

A minimal length of 9 residues for these potential epitopes was set. Following these rules, six series of consecutive long-chain residues (side chains of two carbons or more) located between molecular spacers and/or molecular bends were found (Table 4).

Five of six series that were identified by these rules fit amino acid sequences that were found to be experimentally recognized by B-cell antibodies (Table 4). Consequently, in order to find more epitopes, the program was run with a slight change, namely search of epitopes that contain at most one molecular spacer (G, S or A). The minimal length was set at 12 residues (instead of 9 previously) in order to lower the background (i.e., a penalty of three residues was set to compensate the gap). Two new sequences were identified, that were also found to be experimentally recognized by B-cell antibodies (peptides 31, 45; see Table 4). The molecular spacer was glycine in these two cases.

In order to better understand the implications of the tertiary structure of MT HSP 65KD and to locate these different amino acid sequences on the whole molecule, a model for the tertiary structure of MT HSP 65KD based on the crystal structure of E. coli GroEL (FIG. 3) was used.

Structure analysis confirmed that the experimentally recognized epitopes located on the surface of the protein can provide a potential site to antibodies binding. Peptides 6, 7, 21, 31, 59 were those that were found to be the most exposed whereas peptides 36, 40, 45, 63 and 84 are partially exposed.

The single potential epitope that was not recognized experimentally (residues 318-331) seems to be "Buried" in the molecule.

Although there is a marked homology between MT HSP 65KD and mammalian HSP 60KD, most of the peptides that were found to be recognized by the anti-MT HSP 65 antibodies did not show high residues homology with the mammalian HSP. This may be due to the tolerance to self that protects the rats from developing an autoimmune autoantibody response to their own HSP 60. Two peptides, 6 and 45, did not seem to conform to this rule as they had sites showing high homology to the self HSP.

These findings may be explained for both peptides as follows:

As to peptide 6 (residues 31-46): antibodies were found to bind peptide 7 (residues 37-52) which overlap the polymorphic part of this peptide, and the mammalian peptide 5 (residues 61-80) representing the region homologous with the mammalian HSP. It seems, that these antibodies are directed against the polymorphic (non-self) region of peptide 6 (residues 40-46). It can also provide a hypothesis concerning the

TABLE 4

Potential epitopes of MT HSP 65KD

| Location of the peptide (aa residues) | Sequence of the peptide | Length | SEQ ID NO. | Experimental peptide matching |
|---|---|---|---|---|
| 35-43 | G-RNVVLEKKW-G | 9 | 18 | 6, 7 |
| 123-132 | A-VEKVTETLLK-G | 10 | 19 | 21 |
| 135-143 | A-KEVETKEQI-A | 9 | 20 | 21 |
| 319-332 | RKVVVTKDAETTIVE | 14 | 21 | none |
| 357-367 | S-DYDREKLQERL-A | 11 | 22 | 59 |
| 383-396 | A-TEVELKERKHRIED-A | 14 | 23 | 63 |
| 183-195 | G-LQLELTEGMRFDK-G | 13 | 24 | 31 |
| 259-270 | S-TLVVNKIRQTFK-S | 12 | 25 | 45 |

"protective" ability of this peptide, partial homology to the mammalian HSP 60 sequence may be responsible for this protective effect.

As to peptide 45 (residues 265-280): This peptide can be divided into two consecutive regions: one polymorphic (residues 265-271) and the second highly conserved (residues 271-280). Analysis of the three-dimensional structure shows that the polymorphic region is the exposed region, whereas the conserved region seems to be "buried" in the whole molecule (not shown). Therefore, it is possible that the antibodies that bind peptide 45 are mainly directed against the exposed polymorphic region.

No particularity concerning the secondary structure and the repartition of hydrophobic/polar residues in these epitopes was noticed (both experimentally and computer recognized). Generally, the experimentally recognized epitopes tend to be hydrophobic (9-12 hydrophobic residues out of 16), but for peptide 59 that is highly polar (13 residues out of 16).

With reference to the Figures, FIG. 2 shows the location of bacterial peptides 6, 7 and 31 on the three dimensional structure of the *E. Coli* GroEL-GroES complex and FIG. 3, as stated, shows the same peptides on a model of the MT HSP 65 based on the structure of GroEL *E. Coli* with a space-filling and secondary structure representations.

Example 4

Analysis of the Ability of Peptides to Immunize Against AA

To test whether active immunization with bacterial or mammalian HSP peptides that are recognized by protective immunoglobulins can induce protection against AA, Lewis rats were immunized with the mycobacterial peptides 6, 7, 21, 31, 36, 45, 84, that bound antibodies from resistant Lewis rats ("protective" peptides), with some non-reactive mycobacterial HSP 65 peptides: peptide 26 (residues 151-166), 28 (residues 163-178) or peptide 70 (residues 415-430), and with the mammalian peptide 5.

Rats were injected 3 times intraperitoneally (IP), with one week intervals between injections before induction of AA with MT.

FIG. 4 shows that only pre-immunization of rats with the bacterial peptides 6 and 7 and the mammalian peptide 5 resulted in a significant suppression of disease severity.

Immunization with these "protective" peptides also resulted in the production of antibodies against peptide 6 as well as against the whole MT HSP 65 (Table 5).

TABLE 5

Anti HSP Antibodies in Immunized Lewis Rats

| Immunizing Peptide | Antigen | | | |
|---|---|---|---|---|
| | 6 | 7 | M5 | MT-HSP 65 |
| PBS | − | − | − | − |
| 6 | ++ | − | − | ++ |
| 7 | + | − | − | + |
| M5 | + | − | − | + |

O.D.: <0.15 = −; 0.16-0.45 = +; 0.46-0.75 = ++; >0.75 = +++

Example 5

Analysis of the Ability of Peptide 6 to Immunize Against Autoimmune Diabetes

To test whether active immunization with the bacterial HSP peptide 6 (SEQ ID: NO. 2) can induce protective immunoglobulins against other autoimmune disorders, for instance autoimmune diabetes, NOD mice were immunized with the mycobacterial peptide 6 ("protective" peptide).

Naive NOD mice were immunized 3 times I.D. with either 100 µg peptide 6 in CFA and IA or PBS (control). Mice were monitored for the onset of diabetes by glucose test (appearance of hyperglycemia) and for anti-peptide 6 or anti-HSP 60 antibodies by ELISA. Mice immunized with the peptide developed anti-peptide 6 as well as anti-HSP 65 antibodies as reflected by OD (1.52±0.07 and 1.43±0.13 respectively) in comparison to CFA immunized mice (0.05±0.01 and 0.01±0.01) and control mice (0.09±0.06 and 0.16±0.16).

FIG. 7 shows that in NOD mice immunized with the bacterial peptide 6, the appearance of the diabetic symptoms was clearly delayed and the disease severity was significantly reduced.

Immunization with this "protective" peptide resulted in the production of antibodies against peptide 6 and against the whole HSP 65, which delayed the appearance of diabetes and significantly lowered the number of sick mice in the peptide-6 vaccinated group.

Example 6

Level of Anti-Peptide 6 and Anti-HSP 65 Antibodies in Diabetic Patients and Healthy Donors The presence of anti-peptide 6 and anti-HSP antibodies in serum samples from normal and diabetic patients (type 1 and type 2) was evaluated. Sera from healthy donors (n=11), type 1 diabetes patients (n=10) and type 2 diabetes patients (n=10) were tested by ELISA for the presence of antibodies that bind to peptide 6 and HSP 65. Anti-peptide 6 antibodies were found to be significantly lower in type 1 diabetes patients (*p<0.05) compared to type 2 diabetes patients or healthy controls (as shown in FIG. 14). The difference between diabetic patients and controls was specific for the type 1 and not for type 2 diabetes patients. Anti-peptide 6 antibodies level was similar in these two groups: type 2 diabetes patients and controls. Although anti-HSP antibody level varied among the groups, the lowest titer was observed in type 1 diabetes patients.

Immunization of NOD mice with the "protective" peptide results in the production of antibodies against peptide 6 and the whole HSP 65. Consequently an attenuation of the disease symptoms can be observed. Consistent with this idea, it was found that patients suffering from type 1 diabetes have low amounts of these antibodies. Therefore, evaluation of the anti-peptide 6 serum titer level may be useful for predicting the predisposition of an individual to develop autoimmune diabetes.

Example 7

Treatment of Autoimmune Arthritis by Protective Antibodies Against a Heat Shock Protein Surface Epitope Resistance to AA is due to the presence of natural as well as acquired anti-heat shock protein (HSP) antibodies. These antibodies are directed against peptide 6, a 16 amino-acid peptide from the bacterial HSP (residues 31-46). As active vaccination with peptide 6 induced anti-peptide 6 antibodies and suppressed the severity of AA, the effect of a passive treatment with a rat anti-peptide 6 monoclonal antibody R53F was tested. Lewis rats were immunized with MT in CFA to induce AA and concomitantly treated with R53F a rat anti-peptide 6 monoclonal antibody, with an unrelated rat monoclonal antibody (R83D) or PBS (control). The antibodies were first administrated IV and IP the following day.

Treatment with R53F, a rat anti-peptide 6 monoclonal antibody, reduced arthritis severity on day 25 (FIG. 8). The rat control unrelated monoclonal antibody R83D, had no significant effect on the severity of AA.

Active vaccination with peptide 6 as well as passive vaccination with monoclonal anti-peptide 6 antibodies suppressed significantly AA in Lewis rats.

Example 8

Rat Monoclonal Anti-Peptide 6 Antibody Modulation Effect on Collagen Arthritis Severity (a Mouse Autoimmune Arthritis Model)

DBA/1 mice induced to develop Collagen arthritis were treated with either anti-peptide 6 monoclonal antibody R34C or PBS (control). Arthritis was evaluated by measuring feet diameter.

Treatment with R34C, a rat anti-peptide 6 monoclonal antibody, reduced arthritis severity (FIG. 9).

Active vaccination with peptide 6 as well as passive vaccination with anti-peptide 6 monoclonal antibody suppressed significantly murine collagen arthritis.

Example 9

The Anti-Inflammatory Effect of Mouse, Rat and Human Anti-Peptide 6 Antibodies Mechanism To test whether the protective action of anti-peptide 6 antibodies is due to their influence on inflammatory cytokines, a series of experiments were performed. The effect of polyclonal and monoclonal anti-peptide 6 antibodies on cytokine secretion was analyzed in vitro.

In previous experiments [Ulmansky, R. et al., J. Immunol. 168:6463-6469 (2002)], supernatant samples collected from human and naive Lewis rats PBMC incubated with LPS, with naive Lewis rat polyclonal IgG or with polyclonal anti-peptide 6 antibodies were tested for IL-10 secretion.

Anti-peptide 6 induced at least a six-fold higher secretion of IL-10 by rat PBMC compared with the control. The effect was specific to the anti-peptide 6 antibodies as IgG from naive Lewis rats did not show a similar effect. Incubation of murine and human mononuclear cells with the protective antibodies induced a significant increase in the secretion of IL-10. The use of a human monoclonal antibody induced 15 fold increase in the secretion of IL-10 by human macrophages. Induction of IL-10 was a direct effect of the interaction of the antibodies with the macrophages and did not require the presence of any HSP antigen.

Example 10

Induction of IL-10 Secretion Upon Incubation with Rat Anti-Peptide 6 R53F Monoclonal Antibody Naive human macrophages were incubated with LPS (10 ng/ml) or with the rat monoclonal anti-peptide 6 R53F antibody (8 and 16 µg/ml). Untreated cells served as control. IL-10 secretion to the medium was measured by ELISA. FIG. 10 shows that IL-10 secretion in the samples incubated with 16 µg/ml R53F antibody was at least 4 times higher than in the control samples.

Induction of IL-10 Secretion Upon Incubation with Mouse Anti-Peptide 6 MF9 Monoclonal Antibody Naive human macrophages were incubated with LPS (10 ng/ml), with the mouse monoclonal anti-peptide 6 MF9 antibody (25 µg/ml) or with a mouse unrelated monoclonal antibody (25 µg/ml). Untreated cells served as control. IL-10 secretion (pg/ml) to the medium was measured by ELISA.

As seen in FIG. 11, the presence of the mouse monoclonal anti-peptide 6 MF9 antibody induced 14-15 fold increase in the secretion of IL-10 by the human macrophages.

Example 11

Binding of Rat Anti-Peptide 6 to Human Macrophages Cell Extract

In order to understand in what manner anti-peptide 6 antibodies induce IL-10 secretion, human macrophage were fractionated to nuclear, cytoplasmic and membrane fractions. The different fractions were resolved by SDS-PAGE and subjected to Western blotting using the monoclonal rat anti peptide 6 (10 µg/ml). The monoclonal antibody showed a 19KD and 30KD nuclear bands and a 19KD band in the membrane fraction (FIG. 12*a*). Polyclonal rat antibodies (10 µg/ml) used as negative controls, did not bind to any of these bands.

The R34C anti-peptide 6 monoclonal antibodies bound specifically to a 30KD surface molecule on the human macrophages membrane.

Purified human macrophages were fractionated to hydrophilic membrane, hydrophobic membrane and cytoplasmic proteins, using a different fractionation method. The different fractions were separated in SDS-PAGE, transferred to nitrocellulose and incubated with a rat anti-peptide 6 hybridoma supernatant (clone B-24).

A 55KD, 100KD and 120KD hydrophilic membrane proteins bands were recognized by this antibody. A 55KD band was also recognized in the cytoplasmic fraction (FIG. 12*b*).

Example 12

Level of Anti-Peptide 6 and Anti-HSP 65 Antibodies in Rheumatoid Arthritis (RA) Patients and Healthy Donors Given the significant evidence shown above to support the anti-peptide-6 approach for the treatment of rheumatoid arthritis, the present inventors next evaluated the levels of anti-peptide-6 antibodies in RA patients in comparison with healthy individuals in order to obtain initial indications for clinical application Sera from healthy donors (n=17) or RA patients (n=25) were tested for antibody binding to peptide 6 and HSP 65 by ELISA and for immunoglobulin G levels. Anti-peptide 6 antibodies were found to be significantly lower (by 3 fold) in the RA patients (*$p<0.01$) when compared to control samples (as shown in FIG. 13). This difference between RA patients and control was specifically for anti-peptide 6 antibodies, since total immunoglobulin G amounts, as well as anti-HSP antibody level, was similar in both groups.

These results are sustained by previously described experiments in animal models for arthritis, in which high level of anti-peptide 6 antibodies in rats prevented the induction of AA. The presence of anti-peptide 6 antibodies confers "protection" from arthritis and therefore passive vaccines based in humanized and human monoclonal anti-peptide 6 antibodies, as well as active vaccines using the peptide itself, should be considered as a new therapeutic approach for Rheumatoid arthritis.

The invention claimed is:

1. A composition comprising as an active ingredient an effective amount of at least one isolated and purified antibody directed against a peptide consisting of the amino acid sequence of SEQ ID NO:1 or against biologically functional homologues and derivatives thereof, wherein the biologically functional homologues and derivatives thereof are selected from the group consisting of SEQ ID NO:2 and SEQ ID NO:3, said composition further comprising a pharmaceutically acceptable carrier, excipient, or diluent.

2. The composition according to claim 1, wherein said antibody is directed against a purified peptide consisting of the amino acid sequence of SEQ ID NO:1.

3. The composition according to claim 1, wherein said antibody is directed against a purified peptide consisting of the amino acid sequence of SEQ ID NO:2.

4. The composition according to claim 1, wherein said antibody is directed against a purified peptide consisting of the amino acid sequence of SEQ ID NO:3.

5. A pharmaceutical composition for treatment or amelioration of inflammatory arthritis, wherein said composition comprises as an active ingredient a therapeutically effective amount of at least one isolated and purified antibody directed against a peptide consisting of the amino acid sequence of SEQ ID NO:1 or against biologically functional homologues and derivatives thereof, wherein the biologically functional homologues and derivatives thereof are selected from the group consisting of SEQ ID NO:2 and SEQ ID NO:3, said composition further comprises a pharmaceutically acceptable carrier, excipient, or diluent.

6. A composition for increasing expression and levels of IL-10 (Interleukine-10), said composition comprising as an active ingredient an effective amount of at least one isolated and purified antibody directed against a peptide consisting of the amino acid sequence of SEQ ID NO:1 or against biologically functional homologues and derivatives thereof, wherein the biologically functional homologues and derivatives thereof are selected from the group consisting of SEQ ID NO:2 and SEQ ID NO:3, said composition further comprising a pharmaceutically acceptable carrier, excipient, or diluent.

7. The composition according to claim 6, wherein the composition is for increasing expression and levels of IL-10 in a subject in need thereof, thereby modulating a Th1/Th2 cell balance towards an anti-inflammatory Th2 response in said subject, wherein said subject is suffering from inflammatory arthritis.

8. A method for treatment or amelioration of inflammatory arthritis comprising a step of administering to a subject in need thereof a therapeutically effective amount of at least one isolated and purified antibody directed against a peptide consisting of the amino acid sequence of SEQ ID NO:1 or against biologically functional homologues and derivatives thereof, or of a composition comprising the same, wherein the biologically functional homologues and derivatives of said peptide are selected from the group consisting of SEQ ID NO:2 and SEQ ID NO:3.

9. A method for increasing expression and levels of IL-10 in a subject suffering from any one of inflammatory arthritis and diabetes, said method comprising a step of administering to said subject a therapeutically effective amount of at least one isolated and purified antibody directed against a peptide consisting of the amino acid sequence of SEQ ID NO:1 or against biologically functional homologues and derivatives thereof, or of a composition comprising the same, wherein the biologically functional homologues and derivatives of said peptide are selected from the group consisting of SEQ ID NO:2 and SEQ ID NO:3.

10. The method according to claim 9, wherein increasing expression and levels of IL-10 leads to modulation of a Th1/Th2 cell balance towards an anti-inflammatory Th2 response in said subject.

11. A purified B cell epitope peptide consisting of the amino acid sequence of SEQ ID NO:1 or biologically functional homologues and derivatives thereof selected from the group consisting of SEQ ID NO:2 and SEQ ID NO:3, wherein said peptide is for treatment and amelioration of inflammatory arthritis and diabetes.

12. A pharmaceutical composition for treatment or amelioration of inflammatory arthritis and diabetes, wherein said composition comprises as an active ingredient a therapeutically effective amount of at least one isolated and purified peptide consisting of the amino acid sequence of SEQ ID NO:1 or biologically functional homologues and derivatives thereof, wherein the biologically functional homologues and derivatives thereof are selected from the group consisting of SEQ ID NO:2 and SEQ ID NO:3, and wherein said composition further comprises a pharmaceutically acceptable carrier, excipient, or diluent.

13. A method for treatment or amelioration of inflammatory arthritis and diabetes comprising a step of administering to a subject in need thereof a therapeutically effective amount of at least one isolated and purified peptide according to claim 11, or of a composition comprising the same.

* * * * *